United States Patent [19]

McLoughlin et al.

[11] Patent Number: 5,223,526
[45] Date of Patent: Jun. 29, 1993

[54] PYRAZOLE CARBOXANILIDE FUNGICIDES AND USE

[75] Inventors: Jim I. McLoughlin, St. Louis; Suzanne Metz, Chesterfield, both of Mo.

[73] Assignee: Monsanto Company, St. Louis, Mo.

[21] Appl. No.: 967,417

[22] Filed: Nov. 5, 1992

Related U.S. Application Data

[63] Continuation-in-part of Ser. No. 936,717, Aug. 31, 1992, abandoned, which is a continuation of Ser. No. 877,907, May 1, 1992, abandoned, which is a continuation-in-part of Ser. No. 802,978, Dec. 6, 1991, abandoned.

[51] Int. Cl.$^5$ ............ A01N 43/56; C07D 231/14; C07D 231/18; C07D 405/12
[52] U.S. Cl. .................. 514/406; 514/407; 548/365.7; 548/369.7; 548/375.1
[58] Field of Search ........... 548/365.7, 369.7, 375.1; 514/406, 407

[56] References Cited

U.S. PATENT DOCUMENTS

| | | | |
|---|---|---|---|
| 4,134,987 | 1/1979 | Huppatz | 548/377 |
| 4,214,090 | 7/1980 | Huppatz | 548/378 |
| 4,742,074 | 3/1988 | Nishida et al. | 514/406 |
| 5,049,575 | 9/1991 | Ohsumi et al. | 514/406 |
| 5,093,347 | 3/1992 | Graneto et al. | 514/406 |

FOREIGN PATENT DOCUMENTS 62-249975 10/1987 Japan .

OTHER PUBLICATIONS

Drouhot et al, "Properties of Botrytis cinerea Mitochondria and Effects of Various Toxicants", *Pest. Science*, 1990, 30:415–60.

*Primary Examiner*—Robert W. Ramsuer
*Attorney, Agent, or Firm*—Grace L. Bonner; Howard C. Stanley

[57] ABSTRACT

Novel N-[2-(cyclic alkyl)phenyl]pyrazole-4-carboxamides useful as fungicides, methods of using said compounds, and fungicidal compositions containing them.

13 Claims, No Drawings

PYRAZOLE CARBOXANILIDE FUNGICIDES AND USE

This application is a continuation-in-part of U.S. Ser. Number 07/936,717, filed Aug. 31, 1992, now abandoned, which is a continuation of U.S. Ser. No. 07/877,907, filed May 1, 1992, now abandoned, which was a continuation-in-part of U.S. Ser. No. 07/802,978, filed Dec. 6, 1991, now abandoned.

FIELD OF THE INVENTION

The present invention provides novel N-[2-(cyclic alkyl)phenyl]pyrazole-4-carboxamides useful as fungicides.

BACKGROUND OF THE INVENTION

Fungicides control various phytopathological diseases by interrupting various metabolic pathways within the fungal organism. Thus different fungicides may control the same disease, but by different modes of action. Many organisms, however, can develop resistance to a particular mode of action over time. Thus, having available fungicides which act by various modes of action is important to adequately control most diseases.

One mode of action is the inhibition of the succinate dehydrogenase (SDH) enzym in the respiratory pathway of fungi. This mode of action has previously been demonstrated for control of basidiomycetes. For example, carboxin is a commercially available fungicide which exhibits this mode of action against various basidiomycetes. Drouhot et al. ["Properties of Botrytis cinerea Mitochondria and Effects of Various Toxicants Including Fungicides," *Pesticide Science*, 30:415–417, 1991] have suggested that such a mode of action for control of ascomycetes, such as Botrytis sp., is needed to overcome resistance problems. In their tests of respiratory inhibition, carboxin exhibited a 68% inhibition at 1 μM concentration and was judged the best fungicide of those tested for SDH mode of action against Botrytis.

Pyrazolecarboxamide fungicides are known in the art. U.S. Pat. No. 4,134,987 (Huppatz, Jan. 16, 1979) discloses various N-(phenyl)pyrazolecarboxamides. U.S. Pat. No. 4,742,074, issued May 3, 1988, to Nishida et al., discloses various N-(substituted-indanyl)-pyrazole-4-carboxamides useful as fungicides for various agronomic diseases.

It is an object of this invention to provide compounds having a high level of activity in SDH inhibition in ascomycetes. It is a further object of this invention to provide compounds having a broad spectrum of activity against fungal diseases of plants. It is a further object of this invention to provide methods of controlling or preventing fungal diseases of plants. It is a still further object of this invention to provide fungicidal compositions useful in carrying out those methods.

SUMMARY OF THE INVENTION

Therefore, the present invention comprises compounds of the formula:

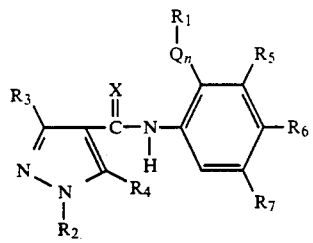

wherein:
Q is C1—C3 alkyl, C2-C3 alkyenyl, C2-C3 alkynyl, $-(CH_2)_m CH=$, or $-(CH_2)_m-X-(CH_2)_m-$;
n is 0 or 1;
each m is independently 0, 1, 2 or 3;
each X is independently O or S;
$R_1$ is C3-C12 cycloalkyl, C3-C12 cycloalkenyl, C6-C12 bicycloalkyl, C3-C12 oxacycloalkyl, C3-C12 oxacycloalkenyl, C3-C12 thiacycloalkyl, C3-C12 thiacycloalkenyl, or C3-C12 cycloalkylamine, each of which may be optionally substituted with one or more C1-8 alkyl, C1-8 alkoxy, halo, or cyano groups, provided that when $-Q-R_1$ is $-(CH_2)_m CH=R_1$, the cycloalkyl of $R_1$ is a cycloalkylidene;
$R_2$ is hydrogen, fluorinated methyl, methyl, ethyl, C2-C6 alkenyl, C3-C6 cycloalkyl, phenyl, alkylthioalkyl, alkoxyalkyl, haloalkylthioalkyl, haloalkoxyalkyl, or hydroxyalkyl;
$R_3$ is halomethyl, halomethoxy, methyl, ethyl, halo, cyano, methylthio, nitro, aminocarbonyl, or aminocarbonylmethyl;
$R_4$ is hydrogen, halo, or methyl;
$R_5$, $R_6$, and $R_7$ are each independently selected from hydrogen, halo, cyano, C1-6 alkyl, C2-C6 alkenyl, C2-C6 alkynyl, C1-C4 alkylthio, C3-C4 cycloalkyl, and halomethoxy.

The present invention also provides methods of controlling or preventing fungal diseases of plants by applying one or more compounds as just described to the plant locus. The present invention also provides fungicidal compositions comprising one or more of the compounds just described and one or more adjuvants.

In the present invention it is preferred that n is O, $R_2$ is methyl, $R_3$ is fluorinated methyl, and $R_4$ is hydrogen.

As used herein, the term "alkyl", unless otherwise indicated, means an alkyl radical, straight or branched chain, having, unless otherwise indicated, from one to ten carbon atoms. The terms "alkenyl" and "alkynyl" mean unsaturated radicals having from two to six carbon atoms. Examples of such alkenyl groups include ethenyl, 1-propenyl, 2-propenyl, 1-butenyl, 2-butenyl, 3-butenyl, 2-methyl-1-propenyl, 2-methyl-2-propenyl, 1-methylethenyl, and the like. Examples of such alkynyl groups include ethynyl, 1-propynyl, 2-propynyl, 1,1-dimethyl-2-propynyl, and so forth.

As used herein, the term "cycloalkyl" means a cyclic alkyl radical having from three to twelve carbon atoms. Examples of such cycloalkyl groups include cyclopropyl, cyclobutyl, cyclopentyl, cyclohexyl, cycloheptyl, cyclooctyl, and so forth. As used herein, the term "cycloalkenyl" means an unsaturated cyclic radical having from three to twelve carbon atoms. The radical may contain more than one double bond. Examples of such cycloalkenyl groups include cyclopropenyl, cyclobutenyl, cyclopentenyl, cyclohexenyl, cycloheptenyl, cyclooctenyl, and so forth.

As used herein, the term "bicycloalkyl" means a cyclic alkyl radical having from six to twelve carbon atoms which comprise more than one ring structure. Examples of such cycloalkyl groups include norbornyl (bicyclo[2.2.1]heptyl).

As used herein, the terms "oxacycloalkyl" and "oxacycloalkenyl" mean cyclic alkyl and alkenyl radicals having from three to twelve carbon atoms, one of which has been replaced by an oxygen. Examples are oxanyl, oxepanyl, oxocanyl, oxinyl, oxepinyl, oxocinyl, etc.

As used herein, the terms "thiacycloalkyl" and "thiacycloalkenyl" mean cyclic alkyl and alkenyl radicals having from three to twelve carbon atoms, one of which has been replaced by a divalent sulfur atom. Examples are thianyl, thiepanyl, thiocanyl, thiinyl, thiepinyl, thiocinyl, etc.

As used herein, the term "cycloalkylamine" means a cyclic alkyl radical having from three to twelve carbon atoms, one of which has been replaced by a divalent —NH— group forming a secondary amine or a divalent alkylamine group forming a tertiary amine. Examples are perhydroazinyl, perhydroazepinyl, perhydroazocinyl, etc., and N-methylperhydroazinyl, N-methylperhydroazepinyl, N-methylperhydroazocinyl, etc.

As used herein, the term "alkoxy" means an alkyl group having, unless otherwise indicated, from one to six carbon atoms connected via an ether linkage. Examples of such alkoxy groups include methoxy, ethoxy, propoxy, 1-methylethoxy, and so forth.

As used herein, the term "alkoxyalkyl" means an ether radical having, unless otherwise indicated, from one to ten carbon atoms. Examples of such alkoxyalkyl groups include methoxymethyl, methoxyethyl, ethoxymethyl, ethoxyethyl, and so forth.

As used herein, the term "fluorinated methyl" means a methyl radical having one or more hydrogen atoms replaced by fluorine atoms, including radicals having all hydrogen atoms substituted by fluorine, i.e., fluoromethyl, difluoromethyl, and trifluoromethyl.

As used herein, the term "halo" means a radical selected from chloro, bromo, fluoro, and iodo. As used herein, the terms "halomethyl" or "halomethoxy" mean that one or more of the hydrogen atoms have been replaced by halogen atoms, including methyl or methoxy groups having all hydrogen atoms substituted with halogens. The term also includes mixed halogen substitution, for example, chlorodifluoromethyl.

As used herein, the term "alkylthioalkyl" means a thioether radical having, unless otherwise indicated, from one to ten carbon atoms. Examples of such alkylthioalkyl groups include methylthiomethyl, methylthioethyl, ethylthiomethyl, ethylthioethyl, and so forth.

DETAILED DESCRIPTION OF THE INVENTION

Most of the compounds of the present invention may be easily prepared by coupling the desired 4-pyrazolecarbonyl chloride with the desired aniline. The following synthetic methods exemplify the ways in which the 4-pyrazolecarbonyl chloride compounds and the anilines may be prepared and coupled. Other compounds of the present invention may be derived from the carboxanilides so prepared. The following abbreviations have the meanings shown:

| RT | room temperature |
| RC | radial chromatography |
| h | hour(s) |
| min | minute(s) |
| DMSO | dimethylsulfoxide |
| THF | tetrahydrofuran |
| EtOAc | ethyl acetate |

Anilines

2-Cyclooctylaniline: Aniline (27.9 g, Aldrich), cyclooctene (33.0 g, Aldrich) and 'F-6' grade clay (9.2 g, Engelhard) were heated in a stirred autoclave for 10 h at 210° C. The dark product was filtered and volatile materials were removed in vacuo (60° C., 40 mm). The oil was distilled (Kugelrohr, 110–140 ° C., 0.5 mm) to give 41.2 g of a viscous yellow oil. The product was chromatographed on silica (Waters 500 A, preparative liquid chromatograph) with EtOAc and hexane to give 2-cyclooctylaniline as a viscous yellow oil (31.0 g).

The following 2-cycloalkylanilines were prepared a described above for 2-cyclooctylaniline. Appropriately substituted anilines and cycloalkenes were commercially available (Aldrich) and used without additional purification.

2-cyclohexylaniline
2-cyclopentylaniline
2-cycloheptylaniline
2-(exo)bicyclo[2.2.1]heptylaniline
2-cyclohexyl-3-fluoroaniline
2-cyclohexyl-4-fluoroaniline
2-cyclohexyl-5-fluoroaniline
2-cyclohexyl-3-methylaniline
2-cyclohexyl-4-methylaniline
2-cyclohexyl-5-methylaniline
2-cyclopentyl-3,5-dimethylaniline
2-cyclohexyl-5-methoxyaniline
2-cyclooctyl-3-methoxyaniline
2-cyclooctyl-5-methoxyaniline
2-(1-methylcyclopentyl)aniline
2-(1-2methylcyclohexyl)-4-fluoroaniline
2-(3-methylcyclohexyl)aniline 2-(1-Methylcyclopentyloxy)aniline: Sodium hydride (4.0 g, 60% oil dispersion, Aldrich) was rinsed three times with dry hexane under nitrogen. Diglyme (40 mL, anhydrous, Aldrich) was added. The slurry was rapidly stirred at RT and 1-methylcyclopentanol was added dropwise. The slurry was warmed to 80° C. for 30 min then cooled to RT. 2-Fluoronitrobenzene (14.1 g) was added, and the mixture was heated at reflux for 2 h. The product was extracted with ether. The ether phase was washed with water, dried with brine, separated, and dried over $K_2CO_3$. The solution was filtered and concentrated in vacuo to give a light yellow oil. 2-(1-Methylcyclopentyloxy)nitrobenzene was distilled (Kugelrohr, 100° C., 0.5 mm) following distillation of diglyme to give a light yellow oil (21.0 g). The nitro compound was dissolved in ethanol (20 mL, absolute) and 5% Pd on charcoal (0.1 g) was added. The slurry was shaken on a Parr hydrogenation apparatus at 40 psi hydrogen for 16 h. The sample was filtered and concentrated to give the aniline.

The following 2-cycloalkoxyanilines or 2-cycloalkylthioanilines were prepared as described above for 2-(1-methylcyclopentyl)oxyaniline from commercially available alcohols or thiols.

2-(cyclohexyloxy)aniline
2-(cyclopentylmethoxy)aniline
2-(2-cyclopentylethoxy)aniline
2-(3-cyclopentylpropoxy)aniline
2-(cyclobutylmethoxy)aniline
2-(cyclohexylthio)aniline
2-(cyclohexyloxy)-5-methylaniline
2-[(exo)-bicyclo[2.2.1]heptyloxy]aniline
2-[(endo)-bicyclo[2.2.1]heptyloxy]aniline The following 2-cycloalkoxyanilines were prepared as described above for 2-(1-methylcyclopentyloxy)aniline from commercially available diasteriomeric mixtures of alcohols. The diasteriomers were separated via chromatography on silica (Waters 500 A, preparative liquid chromatograph) with EtOAc and hexane. Stereochemical assignments were based upon coupling constants in the proton NMR in CDCl$_3$.

2-(4-methylcyclohexyloxy)aniline
2-(2,6-dimethylcyclohexyloxy)aniline 2-(1-Cyclopentylideneethyl)aniline and 2-(1-cyclopentylethenyl)aniline: To a stirred solution of 2-acetylaniline (27.2 g, Aldrich) in ether at 0° C. was added cyclopentylmagnesium chloride (205 mL, 2.0 M in ether, Aldrich). The yellow solution was stirred overnight while warming to RT. Water was carefully added, and the product was extracted with several portions of ether. The combined ether materials were dried with MgSO$_4$, filtered and concentrated in vacuo. Distillation (Kugelrohr, 130° C., 0.5 mm) gave the alcohol (24.3 g) as a thick amber oil. The alcohol (15.1 g) was stirred with DMSO (100 mL, anhydrous, Aldrich) at reflux for 4 h. The solution was cooled and the products extracted with ether and hexanes. The organic extracts were washed with water, saturated NaHCO$_3$ and brine, then dried with MgSO$_4$. The solution was filtered and concentrated in vacuo. The olefinic products were obtained as a 3:2 ratio of 2-(1-cyclopentylideneethyl)aniline and 2-(1-cyclopentylethenyl)aniline. Chromatography on silica (Waters 500A, preparative liquid chromatograph) with EtOAc and hexane failed to separate the mixture and gave the products as a clear, light yellow oil (8.94 g). The mixture was used directly for formation of carboxanilide products which were then separated.

2-(1-Cyclohexenyl)aniline: To cyclohexanone (24.4 mL) and 2,6-di-t-butyl-4-methylpyridine (48.3 g) in CH$_2$Cl$_2$ (700 mL) at 0° C. was added dropwise triflic anhydride (42 mL) in CH$_2$Cl$_2$ (100 mL). The mixture was stirred overnight slowly coming to RT. A white solid was filtered and the filtrate was concentrated in vacuo. The residue was triturated with hexanes and filtered. The filtrate was concentrated in vacuo. The residue was chromatographed on silica gel eluting with hexanes to give O-trifluoromethylsulfonyl-1-cyclohexenol.

To N-Boc-aniline (30.8 g) in THF (300 mL) at −78° C. was added dropwise t-butyl lithium (1.7 M in pentane, 226 mL). The mixture was warmed to −22 ° C. for 2 h and cooled back down to −78° C. Trimethyltin chloride (67.4 g) in THF (200 mL) was added dropwise. The reaction mixture was stirred overnight, slowly coming to RT, and then partitioned between ether and ice water. The ether layer was dried (MgSO$_4$) and concentrated in vacuo. The residue was chromatographed on silica gel eluting with 10% EtOAc/hexanes.

O-Trifluoromethylsulfonyl-1-cyclohexenol (6.9 g), prepared above, triphenylarsine (0.77 g), tris(dibenzylideneacetone)dipalladium (0.28 g), and N-Boc-(2-trimethyltin)aniline (10.7 g) were mixed in N-methylpyrrolidinone (100 mL) and stirred overnight. The reaction mixture was then washed with water (2×100 mL), stirred with saturated aqueous KF (150 mL) for 0.5 h, dried (MgSO4), and concentrated in vacuo. The residue was chromatographed on silica gel eluting with 5% EtOAc/hexanes, to give N-Boc-2-(1-cyclohexenyl)aniline.

To N-Boc-2-(1-cyclohexenyl)aniline (15 g) in CH$_2$Cl$_2$ (15 mL) at 0° C. was added dropwise trifluoroacetic acid (15 mL). The mixture was stirred overnight coming to RT and concentrated in vacuo. The residue was partitioned between CH$_2$Cl$_2$ and water while adjusting the aqueous layer to pH 9 with 2.5N NaOH. The CH$_2$Cl$_2$ layer was dried (MgSO4) and concentrated in vacuo leaving an oil (10.3 g) which was distilled (Kugelrohr) at 75–85° C. (0.25 mm) to give pure 2-(1-cyclohexenyl)aniline as a clear colorless oil (8.6 g).

The following were prepared as described above using the appropriate ketone starting material:

2-(1-cyclopentenyl)aniline
2-(1-cycloheptenyl)aniline
2-(1-cyclooctenyl)aniline
2-(2-methyl-1-cyclopentenyl)aniline
2-(5,5-dimethyl-1-cyclopentenyl)aniline
2-(2,6-dimethyl-1-cyclohexenyl)aniline
2-(3,3,5,5-tetramethyl-1-cyclohexenyl)aniline
2-(4-ethyl-1-cyclohexenyl)aniline
2{2-(2-[(1-methyl)ethyl]-1-cyclohexenyl}aniline
2-[6-[(1-methyl)ethyl]-1-cyclohexenyl]aniline
2-[4[(1,1-dimethyl)ethyl]-1-cyclohexenyl]aniline
2-(6-ethyl-2-methyl-1-cyclohexenyl)aniline
2-{6-[(1,1-dimethyl)ethyl]-1-cyclohexenyl}aniline
2-(5,6-dihydro-2H-pyran-4-yl)aniline
2-(5,6-dihydro-2H-thiopyran-4-yl)aniline
2-(3-methyl-1-cyclopenten-1-yl)aniline
2-(4-methyl-1-cyclopenten-1-yl)aniline 2-{[4-(1,1-dimethyl)ethyl]cyclohexyl}aniline: 2-{[4-(1,1-dimethyl)ethyl]-1-cyclohexenyl}aniline (3 g), prepared as above, platinum oxide (200 mg), glacial acetic acid (1 mL), and ethanol (50 mL) were shaken on a Parr hydrogenation apparatus under 60 lbs of hydrogen overnight. Contents were filtered and the filtrate was concentrated in vacuo leaving an oil (2.8 g). The oil was purified by chromatography on silica gel eluting with 7.5% EtOAc/hexanes, to give pure 2-{[4-(1,1-dimethyl)ethyl]cyclohexyl}aniline. Earlier fractions were enriched in the trans isomer and later fractions were enriched in the cis isomer.

Also prepared by this method was:
2-[(3,3,5,5-tetramethyl)-1-cyclohexyl]aniline 2-(Cyclohexylidenemethyl)aniline: To a slurry of cyclohexyl triphenylphosphonium bromide (16.6 g) in THF (100 mL) at 24° C. was added potassium t-butoxide (4.38 g). The mixture was stirred for 30 min. o-Nitrobenzaldehyde (3.93 g) in THF (50 mL) was added dropwise below 30° C. and stirred for 30 min. The mixture was then partitioned between EtOAc and ice water. The EtOAc layer was washed well with water, dried (MgSO$_4$) and concentrated in vacuo. The residue was chromatographed on silica gel with 5% EtOAc/hexanes to give 1-(cyclohexylidenemethyl)-2-nitrobenzene.

To 1-(cyclohexylidenemethyl)-2-nitrobenzene (1.6 g) in glacial acetic acid (50 mL), at 85° C., was added iron powder (2.07 g). The mixture was refluxed for 15 min. The mixture was cooled and filtered through clay. The filtrate was partitioned between EtOAc and ice water.

The ethyl acetate layer was washed well with a saturated NaHCO$_3$ solution, dried (MgSO$_4$), and concentrated in vacuo. The residue was chromatographed on silica gel eluting with hexanes to give 2-(cyclohexylidenemethyl)aniline.

The following 2-(cycloalkylidenemethyl)anilines were prepared as described above:
2-(cycloheptylidenemethyl)aniline
2-(cyclopentylidenemethyl)aniline In the preparation of 1-(cyclopentylidenemethyl)-2-nitrobenzene, its isomer, 1-[(cyclopent-1-enyl)methyl]-2-nitrobenzene, was also isolated and then converted to 2-[(cyclopent-1-enyl)methyl]aniline.

2-(Cyclohexylmethyl)aniline: 1-(Cyclohexylidenemethyl)-2-nitrobenzene (3.45 g), prepared as above, glacial acetic acid (30 mL), ethanol (50 mL), and a catalytic amount of 10%Pd/C were shaken on a Parr Hydrogenator under a atmosphere of hydrogen at 23° C. for 24 h. The mixture was filtered through clay and concentrated in vacuo. The residue was chromatographed on silica gel eluting with 10% EtOAc/hexanes to give 2-(cyclohexylmethyl)aniline.

The following 2-(cycloalkylmethyl)anilines were prepared as described above:
2-(cycloheptylmethyl)aniline
2-(cyclopentylmethyl)aniline 5-Chloro-2-cyclohexylaniline: To 1-chloro-4-cyclohexylbenzene (1.7 g) in H$_2$SO$_4$ (10 mL) at 20° C. added HNO$_3$ (2.5 g) in H$_2$SO$_4$ (10 mL) maintaining the temperature below 30° C. The mixture was allowed to stir for 1 h and then partitioned between CH$_2$Cl$_2$ and water. The CH$_2$Cl$_2$ layer was washed well with a saturated NaHCO$_3$ solution, dried (MgSO$_4$), and concentrated in vacuo. The residue was chromatographed on silica gel eluting with 5% EtOAc/hexanes to give 5-chloro-2-cyclohexyl-1-nitrobenzene. This compound was then reduced with iron powder as described above to yield the desired compound.

2-Cyclohexyl-3.5-dibromoaniline: To 4-cyclohexylaniline (10 g), CuBr (9.4 g) and CuBr$_2$ (20.9 g) in acetonitrile (200 mL) was added dropwise a 90% t-butyl nitrite solution (16.9 mL) at 30° C. The mixture was stirred for 1 h and concentrated in vacuo. The residue was taken up in EtOAc and washed with 10% HCl, dried (MgSO$_4$), and concentrated in vacuo. The residue was chromatographed on silica gel eluting with hexanes to give a mixture of 4-bromo-1-cyclohexylbenzene and 1-cyclohexyl-2,4-dibromobenzene.

To this mixture (2.8 g) in H$_2$SO$_4$ (18 mL) at 20° C. was added HNO$_3$ (11.8 mL) in H$_2$SO$_4$ (11.8 mL) maintaining the temperature below 30° C. The mixture was allowed to stir for 1 h and then partitioned between CH$_2$Cl$_2$ and water. The CH$_2$Cl$_2$ layer was washed well with a saturated NaHCO$_3$ solution, dried (MgSO$_4$), and concentrated in vacuo. The residue was chromatographed on silica gel eluting with hexanes to give 2-cyclohexyl-3,5-dibromo-1-nitrobenzene. This compound was then reduced with iron powder as described above to yield the desired compound.

Pyrazoles

Ethyl 3-cyano-1-methyl-1-H-pyrazole-4-carboxylate: To ethyl 3-(carboxaldehyde)-1-methyl-1-H-pyrazole-4-carboxylate, (7.8 g) in ethanol at 0° C. was added hydroxylamine hydrochloride (3.3 g). The material was concentrated in vacuo; chloroform was added and removed in vacuo to assure removal of all of the ethanol. The white-yellow solid was stored under vacuum at RT. A slurry was formed in CH$_2$Cl$_2$ (150 mL, anhydrous). The slurry was cooled to 0° C. and pyridine (10.4 mL) was added followed by the careful addition of trifluoroacetic anhydride (15.7 mL). The solution was stirred 1 h at RT, then 3 h at reflux. The product was extracted with CH$_2$Cl$_2$. The organic material was washed with saturated NaHCO$_3$ and brine then separated and dried with MgSO$_4$. Filtration and concentration in vacuo gave the crude product (7.4 g). Chromatography on silica with hexane, EtOAc, and CH$_2$C$_2$ afforded the desired product (3.1 g).

Ethyl 3-(trifluoromethyl)-1-methyl-1H-pyrazole-4-carboxylate: To ethyl 2-(ethoxymethylene)-4,4,4-trifluoromethyl acetoacetate (132 g, prepared according to JACS 73: 3684, 1951) in ethanol (600 mL) at 0° C., methyl hydrazine (29 mL) in ethanol (100 mL) was slowly added dropwise. After addition was complete, the contents were heated at reflux for 2 h. Stirring continued overnight while the contents cooled to RT. The yellow precipitate was filtered to give the pure desired product (21 g). The filtrate was concentrated in vacuo leaving a yellow oil (81.6 g). The oil was distilled (Kugelrohr 50° C., 0.025 mm) to give the N-methyl isomer of the desired compound (30 g) as a yellow oil. The distillation was continued (80° C., 0.025 mm) to give additional desired product as a yellow solid (35.8 g).

The following 1H-pyrazole-4-carboxylic acid esters were prepared as described above. The appropriate ethyl 2-(ethoxymethylene)acetoacetates were prepared as described in JACS, 73: 3684, 1951, using the appropriate commercially available ethyl acetoacetates.

Ethyl 3-(difluoromethyl)-1-methyl-1H-pyrazole-4-carboxylate
Ethyl 1,3-dimethyl-1H-pyrazole-4-carboxylate
Ethyl 3-(difluoromethyl)-1H-pyrazole-4-carboxylate
Ethyl 1,3,5-trimethyl-1H-pyrazole-4-carboxylate
Ethyl 3-(chlorodifluoromethyl)-1-methyl-1H-pyrazole-4-carboxylate
Ethyl 1,5-dimethyl-3-trifluoromethyl-1H-pyrazole-4-carboxylate Ethyl 3-(difluoromethyl)-1-(2-propenyl)-1H-pyrazole-4-carboxylate: To a solution of potassium hydroxide (3.5 g) in ethanol (50 mL) at 0° C. was added dropwise the ethyl ester of 3-(difluoromethyl)-1H-pyrazole-4-carboxylic acid (10.1 g) in ethanol (50 mL), followed by dropwise addition of allyl bromide (4.6 mL). The mixture was stirred overnight, partitioned between ether and 2N HCl. The ether layer was dried (MgSO$_4$) and concentrated in vacuo leaving an oil (11.4 g). The oil was distilled (Kugelrohr 80–85 ° C., 0.3 mm) to give the isomer of the desired product as an oil (2.6 g). Distillation was continued (100–105 ° C., 0.3 mm) to give the desired compound as a clear colorless oil (8.0 g).

Ethyl 3-(methylthio)-1-methyl-1H-pyrazole-4-carboxylate: To the ethyl ester of 3-amino-1-methyl-1H-pyrazole-4-carboxylic acid (10 g, prepared as in U.S. Pat. No. 3,098,075) and methyl disulfide (7.5 mL) in CH$_3$CN (80 mL) was added dropwise t-butyl nitrite in CH$_3$CN (20 mL). The contents were stirred overnight and partitioned between water and ether. The ether layer was dried (MgSO$_4$) and concentrated in vacuo leaving an amber solid (13.5 g). The solid was recrystallized from EtOAc/hexanes to give the desired ester as a light amber solid (8.0 g).

Ethyl 3-bromo-1-methyl-1H-pyrazole-4-carboxylate was prepared as described above for ethyl 3-(methylthio)-1-methyl 1H-pyrazole-4-carboxylate using copper-(II) bromide.

Ethyl 3-chloro-1-methyl-1H-pyrazole-4-carboxylate was prepared as described above for ethyl 3-(methylthio)-1-methyl-1H-pyrazole-4-carboxylate using copper-(II) chloride.

Ethyl 3-iodo-1-methyl-1H-pyrazole-4-carboxylate was prepared as described above for ethyl 3-(methylthio)thio)-1-methyl-1H-pyrazole-4-carboxylate using iodine in place of methyl disulfide.

Ethyl 1,3-bis-(difluoromethyl)-1H-pyrazole-4-carboxylate: Into a solution of ethyl 3-(difluoromethyl)-1H-pyrazole-4-carboxylate (5.6 g) in DMF (200 mL) at 0° C. was bubbled chlorodifluoromethane (26 g). Sodium hydroxide (50%, 24 g) was added dropwise. The contents were stirred overnight coming to RT and partitioned between water and EtOAc. The EtOAc layer was dried (MgSO4) and concentrated in vacuo leaving a light amber oil (5.3 g). Chromatography on silica gel, eluting with a 15% EtOAc/hexanes mixture gave the desired compound in a pure form as a colorless oil (2.1 g).

Ethyl 3-(difluoromethoxy)-1-methyl-1H-pyrazole-4-carboxylate: Into a solution of ethyl 3-hydroxy-1-methyl-1H-pyrazole-4-carboxylate (10.0 g), prepared as above, in DMF (100 mL) at 0° C. was bubbled chlorodifluoromethane (50 g). At 0° C., NaOH (50%, 48 g) was added dropwise and stirred 72 h, coming to RT. The mixture was partitioned between EtOAc and water. The EtOAc layer was dried (MgSO4) and concentrated in vacuo leaving a yellow oil (7.9 g). The oil was chromatographed on silica gel eluting with 40% EtOAc/hexanes to give the desired compound as a light amber oil which solidified (3.4 g).

1-Methyl-3-nitro-1-pyrazole-4-carboxylic acid: To 3-amino-1-methyl-1H-pyrazole-4-carboxamide (4.6 g), prepared according to Helv Chim Acta 42:349 (1959), and sodium nitrite (3.5 g) was added rapidly conc HCl (19 mL). Contents were refluxed 1 h, allowed to cool, and extracted with ether. The ether layer was dried (MgSO4) and concentrated in vacuo leaving the desired compound as a light yellow solid (900 mg).

3-(Trifluoromethyl)-1-methyl-1H-pyrazole-4-carboxylic acid: Ethyl 3-(trifluoromethyl)-1-methyl-1H-pyrazole-4-carboxylate (22.3 g) was added to a solution of sodium hydroxide (4.4 g) in methanol (200 mL). The contents were heated at reflux for 1 h, then cooled and stirred overnight. The contents were concentrated in vacuo and diluted with water. The aqueous solution was made acidic with 2N HCl and the precipitated white solid was filtered to give the desired acid (18.2 g).

The following were prepared as described above using the appropriate pyrazole ester:
3-(Difluoromethyl)-1-methyl-1H-pyrazole-4-carboxylic acid
1,3-Dimethyl-1H-pyrazole-4-carboxylic acid
1,3,5-Trimethyl-1H-pyrazole-4-carboxylic acid
3-(Difluoromethyl)-1-(2-propenyl)-1H-pyrazole-4-carboxylic acid
3-(Methylthio)-1-methyl-1H-pyrazole-4-carboxylic acid
3-Bromo-1-methyl-1H-pyrazole-4-carboxylic acid
3-Cyano-1-methyl-1H-pyrazole-4-carboxylic acid
3-Chloro-1-methyl-1H-pyrazole-4-carboxylic acid
3-Iodo-1-methyl-1H-pyrazole-4-carboxylic acid
3-Methoxy-1-methyl-1H-pyrazole-4-carboxylic acid
3-Difluoromethyl-1-methyl-1H-pyrazole-4-carboxylic acid
1,3-Bis(difluoromethyl)-1H-pyrazole-4-carboxylic acid
3-(Difluoromethoxy)-1-methyl-1H-pyrazole-4-carboxylic acid
3-(Chlorodifluoromethyl)-1-methyl-1H-pyrazole-4-carboxylic acid
1,5-Dimethyl-3-trifluoromethyl-1H-pyrazole-4-carboxylic acid 5-Chloro-1-methyl-3-trifluoromethyl-1H-pyrazole-4-carboxaldehyde: To ethyl 4,4,4-trifluoroacetoacetate (18 mL, Aldrich) in ethanol (200 mL) was added methyl hydrazine (6.6 mL) in ethanol (50 mL). The mixture was refluxed for 16 h and concentrated in vacuo leaving a white solid. Recrystallization from EtOAc/toluene (50:50) gave pure 5-hydroxy-1-methyl-3-trifluoromethyl-1H-pyrazole.

DMF (106 mL) was stirred under $N_2$ while cooling in an ice/salt bath to 0° C. $POCl_3$ (364 mL) was added dropwise at a rate such that the temperature did not rise above 10° C. The mixture was then stirred at 0° C. briefly and 5-hydroxy-1-methyl-3-(trifluoromethyl)-1H-pyrazole (106 g) was added with constant stirring. The mixture was stirred while slowly heating to 90° C. As the temperature approached 90° C. the reaction became exothermic and HCl gas evolved. The temperature rose to reflux. After the exotherm subsided the mixture was heated at gentle reflux for 16 h. The dark amber solution was cooled to RT and then poured onto 3.kg ice with stirring. The mixture was mixed thoroughly with the ice and more ice added to maintain the temperature below 5° C. The resulting slurry was stirred continuously for 4 h with occasional addition of ice to maintain low temperature. The solid was separated from the liquid phase by drawing the aqueous phase through a sintered glass filter tube. The solid was reslurried with water (4×1 L) and then collected by filtration and air dried. The product was recrystallized from hexane which gave the desired compound as white needles (137 g). m.p. 39–41° C. An additional 30 g product was obtained by concentration of the mother liquor.

The following pyrazolecarboxaldehydes were prepared as just described:
5-Chloro-3-difluoromethyl-1-methyl-1H-pyrazole-4-carboxaldehyde
5-Chloro-1,3-dimethyl-1H-pyrazole-4-carboxaldehyde 5-Fluoro-1-methyl-3-trifluoromethyl-1H-pyrazole-4-carboxaldehyde: A suspension of anhydrous KF (4 g) in anhydrous DMF (20 mL) was stirred under $N_2$ and 1-methyl-3-trifluoromethyl-5-chloropyrazole-4-carboxaldehyde (10.6 g) added. The mixture was heated at 150 ° C. for 6 h. The mixture was poured onto ice (250 g) and was mixed thoroughly. The mixture was extracted with ether (5×50 mL). The ether solution was dried (MgSO4) and concentrated in vacuo leaving an amber liquid (10 g). The liquid was distilled under reduced pressure to give one fraction, 8.0 g yellow liquid b.p. 68–74 ° C. @ 0.4 Torr.

The following pyrazolecarboxaldehydes were prepared as described above:
3-Difluoromethyl-5-fluoro-1-methyl-1H-pyrazole-4-carboxaldehyde
1,3-Dimethyl-5-fluoro-1H-pyrazole-4-carboxaldehyde 1-Methyl-3-trifluoromethyl-5-fluoro-1H-pyrazole-4-carboxylic acid: A solution of 1-methyl-3-trifluoromethyl-5-fluoro-pyrazole-4-carboxaldehyde (9.8 g) in acetone (60 mL) was stirred rapidly at RT while a solution of potassium dichromate dihydrate (5.6 g) in water (38 mL) and sulfuric acid (4.6 mL) was added. The mixture was stirred rapidly overnight then diluted with water (150 mL). The mixture was extracted with $CH_2Cl_2$ (6 ×75 mL). The combined organic solution was washed with water, dried ($MgSO_4$), filtered and concentrated in vacuo leaving a light yellow solid (7.2 g). The solid was recrystallized from EtOAc/hexane to give the desired compound as white crystals (3.8 g). m.p. 165–166° C.

By this method the following pyrazolecarboxylic acids were prepared from the pyrazolecarboxaldehydes described above:

5-Chloro-3-difluoromethyl-1-methyl-1H-pyrazole-4-carboxylic acid

5-Chloro-1,3-dimethyl-1H-pyrazole-4-carboxylic acid

3-Difluoromethyl-5-fluoro-1-methyl-1H-pyrazole carboxylic acid 1,3-Dimethyl-5-fluoro-1H-pyrazole-4-carboxylic acid 1-Methyl-3-(trifluoromethyl)-1H-pyrazole-4-carboxylic acid chloride: 3-(Trifluoromethyl)-1-methyl-1H-pyrazole-4-carboxylic acid (21 g) and thionyl chloride (75 mL) were heated at reflux for 1.5 h. The contents were concentrated in vacuo leaving the desired acid chloride as a yellow oil.

This method was used to prepare the acid chloride of each of the pyrazole-4-carboxylic acids prepared above.

3-(Difluoromethyl)-1H-pyrazole-4-carboxylic acid: The ethyl ester of 3-(difluoromethyl)-1H-4-carboxylic acid (10 g) and freshly distilled trimethylsilyl iodide (25 mL) were heated at 90° C. for 4 h. After cooling, the contents were partitioned between ether and ice water. The ether layer was washed with aqueous sodium metabisulfite, dried ($MgSO_4$), and concentrated in vacuo leaving the desired white solid (8 g).

Pyrazole-Aniline Coupling

N-(2-Cyclohexylphenyl)-1-methyl-3-(trifluoromethyl)-1H-pyrazole-4-carboxamide: To 1-methyl-3-(trifluoromethyl)-1H-pyrazole-4-carboxylic acid chloride (1.6 g) in $CH_2Cl_{12}$ (25 mL) at 0° C. was added dropwise a solution of 2-cyclohexylaniline (1.3 g) and triethylamine (1.0 mL) in $CH_2Cl_2$ (25 mL). The contents were stirred overnight, coming to RT. The contents were washed with water, 2N HCl (2×100 mL), dried ($MgSO_4$) and concentrated in vacuo leaving an amber foam (2.9 g). Crystallization from EtOAc/hexane gave the desired amide as white crystals (1.2 g). Most of the compounds of the present invention were made via this coupling procedure.

N-(2-Cyclohexylphenyl)-3-(difluoromethyl)-1H-pyrazole-4-carboxamide: 3-(difluoromethyl)-1H-pyrazole-4-carboxylic acid (2.0 g) and 1,1'-carbonyldiimidazole (2.0 g) were mixed in THF (20mL, anhydrous) and stirred for 1 h. 2-Cyclohexylaniline (2.2 g) was added, and the contents were heated at reflux for 2 h. After cooling to RT, the contents were concentrated in vacuo leaving a foam (3.7 g). The foam was chromatographed on silica gel (Waters Prep 500) eluting with EtOAc and hexanes to give the desired amide as a white foam (750 mg). The foam was crystallized from EtOAc /pentane to give the product as a white solid (510 mg).

Thioamides

N-(2-Cyclohexylphenyl)-3-(difluoromethyl)-1-methyl-1H-pyrazole-4-carbothioamide: N-(2-cyclohexylphenyl)-3-(difluoromethyl)-1-methyl-1H-pyrazole-4-carboxamide (2.0 g) and Lawesson's reagent (2.4 g) were refluxed in toluene (100 mL) for 1 h. Contents were stirred overnight at RT and filtered. The filtrate was concentrated in vacuo leaving a yellow solid which was chromatographed on silica gel eluting with 35% EtOAc/hexanes to give a yellow solid. The solid was recrystallized from EtOAc to give the desired compound as a yellow solid (1.1 g).

By this method the following carbothioamides were prepared from the corresponding carboxamides:

N-(2-Cycloheptylphenyl)-1-methyl-3-(trifluoromethyl)-1H-pyrazole-4-carbothioamide N-(2-Bicyclo[2.2.1]hept-2-ylphenyl)-3-(difluoromethyl)-1-methyl-1H-pyrazole-4-carbothioamide, exo- N-(2-Bicyclo[2.2.1]hept-2-ylphenyl)-3-chloro-1,5-dimethyl-1-methyl-1H-pyrazole-4-carbothioamide, exo Other Compounds N-[2-(1-cyclopentylethyl)phenyl]-1-methyl-3-(trifluoromethyl)-1H-pyrazole-4-carboxamide: A mixture of N-[2-(1-cyclopentylideneethyl)phenyl]-1-methyl-3-(trifluoromethyl)-1H-pyrazole-4-carboxamide trifluoromethyl)-1H-pyrazole-4-carboxamide and N-[2-(1-cyclopentylethenyl)phenyl]-1-methyl-3-(trifluoromethyl)-1H-pyrazole-4-carboxamide (2.5 g), each prepared using the methods described above, were shaken on a Parr Shaker with 5% Pd/C in ethanol (75 mL) under 60 lbs of $H_2$ overnight. Contents were filtered and concentrated in vacuo leaving a white solid (2.44 g). The solid was recrystallized from EtOAc/hexanes to give the desired compound as a white solid (1.3 g).

The following examples of compounds of the present invention were prepared using the methods described above and used in the biological assays described below:

| Example No. | Compound | Melting Pt. (°C.) |
|---|---|---|
| 1 | 1H-pyrazole-4-carboxamide, N-(2-cyclohexylphenyl)-3-(difluoromethyl)-1-methyl- | 132–134 |
| 2 | 1H-pyrazole-4-carboxamide, N-(2-cyclohexylphenyl)-1-methyl-3-(trifluoromethyl)- | 120–122 |
| 3 | 1H-pyrazole-4-carboxamide, N-(2-cyclohexylphenyl)-1,3-dimethyl- | 182–184 |
| 4 | 1H-pyrazole-4-carboxamide, 3-cyano-N-(2-cyclohexylphenyl)-1-methyl- | 161–163 |
| 5 | 1H-pyrazole-4-carboxamide, 3-bromo-N-(2-cyclohexylphenyl)-1-methyl- | 158–160 |
| 6 | 1H-pyrazole-4-carboxamide, N-(2-cyclopentylphenyl)-1,3-dimethyl- | 150–152 |
| 7 | 1H-pyrazole-4-carboxamide, N-(2-cyclopentylphenyl)-3-(difluoromethyl)-1-methyl- | 127–128 |
| 8 | 1H-pyrazole-4-carboxamide, N-(2-cyclopentylphenyl)-1-methyl-3-(trifluoromethyl)- | 147–149 |
| 9 | 1H-pyrazole-4-carboxamide, N-(2-cycloheptylphenyl)-3-(difluoromethyl)-1-methyl- | 116–117 |
| 10 | 1H-pyrazole-4-carboxamide, N-(2-cycloheptylphenyl)-1-methyl-3-(trifluoromethyl)- | 131–132 |
| 11 | 1H-pyrazole-4-carboxamide, N-(2-cyclohexyl-4-fluorophenyl)-3-(difluoromethyl)-1-methyl- | 135–137 |
| 12 | 1H-pyrazole-4 carboxamide, N-(2-cyclohexyl-4-fluorophenyl)-1-methyl-3-(trifluoromethyl)- | 171–172 |
| 13 | 1H-pyrazole-4-carboxamide, N-(2-cycloheptylphenyl)-1,3-dimethyl- | 137–139 |
| 14 | 1H-pyrazole-4-carboxamide, N-(2-cyclohexylphenyl)-3-(difluoromethyl)-1-(2-propenyl)- | 129–131 |
| 15 | 1H-pyrazole-4-carboxamide, N-(2-cyclohexylphenyl)-3-(difluoromethyl)- | 138–140 |

-continued

| Example No. | Compound | Melting Pt. (°C.) |
|---|---|---|
| 16 | 1H-pyrazole-4-carboxamide, N-(2-cyclohexyl-5-fluorophenyl)-3-(difluoromethyl)-1-methyl- | 139-141 |
| 17 | 1H-pyrazole-4-carboxamide, N-(2-cyclohexyl-3-fluorophenyl)-3-(difluoromethyl)-1-methyl- | 141-143 |
| 18 | 1H-pyrazole-4-carboxamide, N-(2-cyclohexyl-5-methylphenyl)-1-methyl-3-(trifluoromethyl)- | 146-147 |
| 19 | 1H-pyrazole-4-carboxamide, N-(2-cyclohexyl-3-methylphenyl)-1-methyl-3-(trifluoromethyl)- | 178-179 |
| 20 | 1H-pyrazole-4-carboxamide, N-(2-cyclohexyl-3-methylphenyl)-3-(difluoromethyl)-1-methyl- | 157-159 |
| 21 | 1H-pyrazole-4-carboxamide, N-(2-cyclohexyl-5-methylphenyl)-3-(difluoromethyl)-1-methyl- | 128-129 |
| 22 | 1H-pyrazole-4-carboxamide, N-[2-(cyclohexyloxy)phenyl]-3-(difluoromethyl)-1-methyl- | 125-126 |
| 23 | 1H-pyrazole-4-carboxamide, N-[2-(cyclohexyloxy)phenyl]-1-methyl-3-(trifluoromethyl)- | 128-129 |
| 24 | 1H-pyrazole-4-carboxamide, N-(2-cyclooctylphenyl)-3-(difluoromethyl)-1-methyl- | 105-107 |
| 25 | 1H-pyrazole-4-carboxamide, N-(2-cyclooctylphenyl)-1-methyl-3-(trifluoromethyl)- | 100-102 |
| 26 | 1H-pyrazole-4-carboxamide, N-(2-bicyclo[2.2.1]hept-2-ylphenyl)-3-(difluoromethyl)-1-methyl-, exo- | 129-130 |
| 27 | 1H-pyrazole-4-carboxamide, N-(2-bicyclo[2.2.1]hept-2-ylphenyl)-1-methyl-3-(trifluoromethyl)-, exo- | 171-173 |
| 28 | 1H-pyrazole-4-carboxamide, N-(2-cyclohexyl-4-methylphenyl)-3-(difluoromethyl)-1-methyl- | 171-172 |
| 29 | 1H-pyrazole-4-carboxamide, N-(2-cyclohexyl-4-methylphenyl)-1-methyl-3-(trifluoromethyl)- | 179-180 |
| 30 | 1H-pyrazole-4-carboxamide, N-(2-cyclohexylphenyl)-1,3,5-trimethyl- | 144-146 |
| 31 | 1H-pyrazole-4-carboxamide, N-(2-cyclopentyl-3,5-dimethylphenyl)-1-methyl-3-(trifluoromethyl)- | 146-148 |
| 32 | 1H-pyrazole-4-carboxamide, N-(2-cyclohexyl-5-methoxyphenyl)-1-methyl-3-(trifluoromethyl)- | 143-145 |
| 33 | 1H-pyrazole-4-carboxamide, N-[2-(1-cyclopentylideneethyl)phenyl]-1-methyl-3-(trifluoromethyl)- | 102-104 |
| 34 | 1H-pyrazole-4-carboxamide, N-[2-(1-cyclopentylethenyl)phenyl]-1-methyl-3-(trifluoromethyl)- | 122-124 |
| 35 | 1H-pyrazole-4-carboxamide, 3-(difluoromethyl)-1-methyl-N-[2-(1-methylcyclopentyloxy)phenyl]- | 141-143 |
| 36 | 1H-pyrazole-4-carboxamide, 1-methyl-N-[2-(1-methylcyclopentyloxy)phenyl]-3-(trifluoromethyl)- | 142-144 |
| 37 | 1H-pyrazole-4-carboxamide, N-(2-cyclooctyl-3-methoxyphenyl)-1-methyl-3-(trifluoromethyl)- | 140-141 |
| 38 | 1H-pyrazole-4-carboxamide, N-(2-cyclooctyl-5-methoxyphenyl)-1-methyl-3-(trifluoromethyl)- | 134-135 |
| 39 | 1H-pyrazole-4-carboxamide, N-(2-cyclohexylphenyl)-1-methyl-3-(methylthio)- | 120-122 |
| 40 | 1H-pyrazole-4-carboxamide, N-[2-(cyclohexylidenemethyl)phenyl]-1-methyl-3-(trifluoromethyl)- | 93-94 |
| 41 | 1H-pyrazole-4-carboxamide, N-(2-cyclooctylphenyl)-1,3-dimethyl- | 132-133 |
| 42 | 1H-pyrazole-4-carboxamide, N-[2-(cyclobutylmethoxy)phenyl]-3-(difluoromethyl)-1-methyl- | 135-136 |
| 43 | 1H-pyrazole-4-carboxamide, N-[2-(cyclobutylmethoxy)phenyl]-1-methyl-3-(trifluoromethyl)- | 111-112 |
| 44 | 1H-pyrazole-4-carboxamide, N-[2-(cyclohexylthio)phenyl]-3-(difluoromethyl)-1-methyl- | 74-76 |
| 45 | 1H-pyrazole-4-carboxamide, N-[2-(cyclohexylthio)phenyl]-1-methyl-3-(trifluoromethyl)- | 88-93 |
| 46 | 1H-pyrazole-4-carboxamide, N-[2-(cyclopentylmethoxy)phenyl]-3-(difluoromethyl)-1-methyl- | 118-120 |
| 47 | 1H-pyrazole-4-carboxamide, N-[2-(cyclopentylmethoxy)phenyl]-1-methyl-3-(trifluoromethyl)- | 97-99 |
| 48 | 1H-pyrazole-4-carboxamide, N-[2-(3-cyclopentylpropoxy)phenyl]-3-(difluoromethyl)-1-methyl- | 114-115 |
| 49 | 1H-pyrazole-4-carboxamide, N-[2-(3-cyclopentylpropoxy)phenyl]-1-methyl-3-(trifluoromethyl)- | 121-123 |
| 50 | 1H-pyrazole-4-carboxamide, 3-chloro-N-(2-cyclohexylphenyl)-1-methyl- | 167-169 |
| 51 | 1H-pyrazole-4-carboxamide, 3-chloro-N-(2-cycloheptylphenyl)-1-methyl- | 157-159 |
| 52 | 1H-pyrazole-4-carboxamide, N-(2-bicyclo[2.2.1]hept-2-ylphenyl)-3-chloro-1-methyl-, exo- | 152-154 |
| 53 | 1H-pyrazole-4-carboxamide, N-[2-(1-cyclopentylethyl)phenyl]-1-methyl-3-(trifluoromethyl)- | 133-135 |
| 54 | 1H-pyrazole-4-carboxamide, N-[2-(2-cyclopentylethoxy)phenyl]-3-(difluoromethyl)-1-methyl- | 101-104 |
| 55 | 1H-pyrazole-4-carboxamide, N-[2-(2-cyclopentylethoxy)phenyl]-1-methyl-3-(trifluoromethyl)- | 114-116 |
| 56 | 1H-pyrazole-4-carboxamide, N-[2-(cyclohexyl)phenyl]-3-iodo-1-methyl- | 164-166 |
| 57 | 1H-pyrazole-4-carboxamide, N-[2-(cycloheptyl)phenyl]-3-iodo-1-methyl- | 144-146 |
| 58 | 1H-pyrazole-4-carboxamide, N-(2-bicyclo[2.2.1]hept-2-ylphenyl)-3-iodo-1-methyl-, exo- | 141-142 |
| 59 | 1H-pyrazole-4-carboxamide, N-(2-cyclohexylphenyl)-3-(difluoromethoxy)-1-methyl- | 130-132 |
| 60 | 1H-pyrazole-4-carboxamide, N-(2-cycloheptylphenyl)-3-(difluoromethoxy)-1-methyl- | 139-140 |
| 61 | 1H-pyrazole-4-carboxamide, N-(2-cyclohexylphenyl)-1,3-bis(difluoromethyl)- | 143-145 |
| 62 | 1H-pyrazole-4-carboxamide, N-(2-cyclohexylphenyl)-1-methyl-3-nitro- | 173-175 |
| 63 | 1H-pyrazole-4-carboxamide, 3-bromo-N-(2-cycloheptylphenyl)-1-methyl- | 161-162 |
| 64 | 1H-pyrazole-4-carboxamide, 3-bromo-N-(2-cyclopentylphenyl)-1-methyl- | 130-132 |
| 65 | 1H-pyrazole-4-carboxamide, N-(2-bicyclo[2.2.1]hept-2-ylphenyl)-3-bromo-1-methyl-, exo- | 129-131 |
| 66 | 1H-pyrazole-4-carboxamide, N-(2-cycloheptylphenyl)-1,3,5-trimethyl- | 138-140 |
| 67 | 1H-pyrazole-4-carboxamide, 1-methyl-N-[2-(1-methylcyclopentyl)phenyl]-3-(trifluoromethyl)- | 152-154 |
| 68 | 1H-pyrazole-4-carboxamide, N-(2-cyclooctylphenyl)-3-iodo-1-methyl- | 134-135 |
| 69 | 1H-pyrazole-4-carboxamide, N-(2-cyclopentylphenyl)-3-iodo-1-methyl- | 147-149 |
| 70 | 1H-pyrazole-4-carboxamide, 1-methyl-N-[2-(3-methylcyclohexyl)phenyl]-3-(trifluoromethyl)-, trans- | 113-115 |

-continued

| Example No. | Compound | Melting Pt. (°C.) |
|---|---|---|
| 71 | 1H-pyrazole-4-carboxamide, N-(2-bicyclo[2.2.1]hept-2-ylphenyl)-1,3-dimethyl-, exo- | 162–164 |
| 72 | 1H-pyrazole-4-carboxamide, 1-methyl-N-[2-[(4-methylcyclohexyl)oxy]phenyl]-3-(trifluoromethyl)-, cis- | 120–122 |
| 73 | 1H-pyrazole-4-carboxamide, 1-methyl-N-[2-[(4-methylcyclohexyl)oxy]phenyl]-3-(trifluoromethyl)-, trans- | 136–138 |
| 74 | 1H-pyrazole-4-carboxamide, 1-methyl-N-[2-[(2,6-dimethylcyclohexyl)oxy]phenyl]-3-(trifluoromethyl)-, (1alpha,2alpha,6alpha)- | 117–119 |
| 75 | 1H-pyrazole-4-carboxamide, 1-methyl-N-[2-[(2,6-dimethylcyclohexyl)oxy]phenyl]-3-(trifluoromethyl)-, (1alpha,2alpha,6beta)- | 156–157 |
| 76 | 1H-pyrazole-4-Carboxamide, 1 methyl-N-[2-[(2,6-dimethylcyclohexyl)oxy]phenyl]-3-(trifluoromethyl)-, (1alpha,2beta,6beta)- | 121–122 |
| 77 | 1H-pyrazole-4-carbothioamide, N-(2-cyclohexylphenyl)-3-(difluoromethyl)-1-methyl | 202–204 |
| 78 | 1H-pyrazole-4-carbothioamide, N-(2-cycloheptylphenyl)-3-(trifluoromethyl)-1-methyl | 147–149 |
| 79 | 1H-pyrazole-4-carboxamide, 1-methyl-N-[2-(3-methylcyclohexyl)phenyl]-3-(trifluoromethyl)-, cis- | 123–126 |
| 80 | 1H-pyrazole-4-carboxamide, N-[2-(bicyclo[2.2.1]hept-2-yloxy)phenyl]-3-(difluoromethyl)-1-methyl-, exo- | 160 |
| 81 | 1H-pyrazole-4-carboxamide, N-[2-bicyclo[2.2.1]hept-2-yloxy)phenyl]-1-methyl-3-(trifluoromethyl)-, exo- | 141 |
| 82 | 1H-pyrazole-4-carboxamide, N-[2-(bicyclo[2.2.1]hept-2-yloxy)phenyl]-3-(difluoromethyl)-1-methyl-, endo- | 127 |
| 83 | 1H-pyrazole-4-carboxamide, 3-(difluoromethyl)-1-methyl-N-[2-(1-methylcyclopentyl)phenyl]- | 152 |
| 84 | 1H-pyrazole-4-carboxamide, N-(2-cyclohexylphenyl)-5-fluoro-1-methyl-3-(trifluoromethyl)- | 146 |
| 85 | 1H-pyrazole-4-Carboxamide, N-(2-bicyclo[2.2.1]hept-2-ylphenyl)-5-fluoro-1-methyl-3-(trifluoromethyl)-, exo- | 157–159 |
| 86 | 1H-pyrazole-4-carboxamide, N-(2-cycloheptylphenyl)-5-fluoro-1-methyl-3-(trifluoromethyl)- | 167–168 |
| 87 | 1H-pyrazole-4-carboxamide, 5-chloro-N-(2-cyclohexylphenyl)-1-methyl-3-(trifluoromethyl)- | 153–155 |
| 88 | 1H-pyrazole-4-carboxamide, N-(2-bicyclo[2.2.1]hept-2-ylphenyl)-5-chloro-1-methyl-3-(trifluoromethyl)-, exo- | 196–197 |
| 89 | 1H-pyrazole-4-carboxamide, 5-chloro-N-(2-cycloheptylphenyl)-1-methyl-3-(trifluoromethyl)- | 170–172 |
| 90 | 1H-pyrazole-4-carboxamide, 3-(chlorodifluoromethyl)-N-(2-cyclopentylphenyl)-1-methyl- | 143–145 |
| 91 | 1H-pyrazole-4-carboxamide, N-[2-bicyclo[2.2.1]hept-2-ylphenyl]-3-(chlorodifluoromethyl)-1-methyl-, exo- | 156–157 |
| 92 | 1H-pyrazole-4-carboxamide, 3-(chlorodifluoromethyl)-N-(2-cycloheptylphenyl)-1-methyl- | 132–134 |
| 93 | 1H-pyrazole-4-carboxamide, N-(5-chloro-2-cyclohexylphenyl)-3-(difluoromethyl)-1-methyl- | 178–180 |
| 94 | 1H-pyrazole-4-carboxamide, N-(5-chloro-2-cyclohexylphenyl)-1-methyl-3-(trifluoromethyl)- | 165 |
| 95 | 1H-pyrazole-4-carboxamide, 3-(difluoromethyl)-N-[4-fluoro-2-(1-methylcyclohexyl)phenyl]-1-methyl- | 169 |
| 96 | 1H-pyrazole-4-carboxamide, N-[2-(cyclohexyloxy)-5-methylphenyl]-3-(difluoromethyl)-1-methyl- | 126 |
| 97 | 1H-pyrazole-4-carboxamide, N-[2-(cyclohexyloxy)-5-methylphenyl]-1-methyl-3-(trifluoromethyl)- | 133 |
| 98 | 1H-pyrazole-4-carboxamide, N-[4-fluoro-2-(1-methylcyclohexyl)phenyl]-1-methyl-3-(trifluoromethyl)- | 203 |
| 99 | 1H-pyrazole-4-carboxamide, N-(2-cycloheptylphenyl)-1,5-dimethyl-3-(trifluoromethyl)- | 145 |
| 100 | 1H-pyrazole-4-carboxamide, N-(2-bicyclo[2.2.1]hept-2-ylphenyl)-1,5-dimethyl-3-(trifluoromethyl)-, exo- | 169 |
| 101 | 1H-pyrazole-4-carboxamide, N-(2-cyclopentylphenyl)-1,5-dimethyl-3-(trifluoromethyl)- | 117 |
| 102 | 1H-pyrazole-4-carbothioamide, N-(2-bicyclo[2.2.1]hept-2-ylphenyl)-3-(difluoromethyl)-1-methyl-, exo- | 213 |
| 103 | 1H-pyrazole-4-carbothioamide, N-(2-bicyclo[2.2.1]hept-2-ylphenyl)-3-chloro-1,5-dimethyl-, exo- | 117 |
| 104 | 1H-pyrazole-4-carboxamide, 3-(difluoromethyl)-N-[2-(5,6-dihydro-2H-pyran-4-yl)phenyl]-1-methyl- | 130 |
| 105 | 1H-py-razole-4-carboxamide, 3-chloro-N-(2-cycloheptylphenyl)-1,5-dimethyl- | 113 |
| 106 | 1H-pyrazole-4-carboxamide, N-(2-bicyclo[2.2.1]hept-2-ylphenyl)-5-chloro-1,3-dimethyl-, exo- | 138 |
| 107 | 1H-pyrazole-4-carboxamide, 5-chloro-N-(2-cycloheptylphenyl)-1,3-dimethyl- | 147 |
| 108 | 1H-pyrazole-4-carboxamide, N-[2-(5,6-dihydro-2H-pyran-4-yl)phenyl]-1-methyl-3-(trifluoromethyl)- | 170 |
| 109 | 1H-pyrazole-4-carboxamide, N-[2-(1-cyclohexen-1-yl)phenyl]-3-(difluoromethyl)-1-methyl- | 103 |
| 110 | 1H-pyrazole-4-carboxamide, N-[2-(1-cyclohexen-1-yl)phenyl]-1-methyl-3-(trifluoromethyl)- | 113 |
| 111 | 1H-pyrazole-4-carboxamide, N-[2-(1-cyclohepten-1-yl)phenyl]-3-(difluoromethyl)-1-methyl- | 119 |
| 112 | 1H-pyrazole-4-carboxamide, N-[2-(1-cyclohepten-1-yl)phenyl]-1-methyl-3-(trifluoromethyl)- | 107 |
| 113 | 1H-pyrazole-4-carboxamide, N-(2-cycloheptylphenyl)-5-fluoro-1,3-dimethyl- | 126–128 |
| 114 | 1H-pyrazole-4-carboxamide, 5-chloro-N-(2-cycloheptylphenyl)-3-(difluoromethyl)-1-methyl- | 112–113 |
| 115 | 1H-pyrazole-4-carboxamide, N-(2-cycloheptylphenyl)-3-(difluoromethyl)-5-fluoro-1-methyl- | 105–107 |
| 116 | 1H-pyrazole-4-carboxamide, N-[2-(cyclohexylidenemethyl)phenyl]-3-(difluoromethyl)-1-methyl- | 101–102 |
| 117 | 1H-pyrazole-4-carboxamide, N-[2-(1-cyclopenten-1-ylmethyl)phenyl]-3-(difluoromethyl)-1-methyl- | 123 |
| 118 | 1H-pyrazole-4-carboxamide, N-[2-(cyclopentylidenemethyl)phenyl]-3-(difluoromethyl)-1-methyl- | 115 |

-continued

| Example No. | Compound | Melting Pt. (°C.) |
|---|---|---|
| 119 | 1H-pyrazole-4-carboxamide, N-[2-(1-cycloocten-1-yl)phenyl]-4-(difluoromethyl)-1-methyl- | 161 |
| 120 | 1H-pyrazole-4-carboxamide, N-[2-(1-cycloocten-1-yl)phenyl]-1-methyl-3-(trifluoromethyl)- | 125 |
| 121 | 1H-pyrazole-4-carboxamide, 3-(difluoromethyl)-1-methyl-N-[2-(3,3,5,5-tetramethyl-1-cyclohexen-1-yl)phenyl]- | 124 |
| 122 | 1H-pyrazole-4-carboxamide, 3-(difluoromethyl)-N-[2-(5,5-dimethyl-1-cyclopenten-1-yl)phenyl]-1-methyl- | 117 |
| 123 | 1H-pyrazole-4-carboxamide, 1-methyl-N-[2-(3,3,5,5-tetramethyl-1-cyclohexen-1-yl)phenyl]-3-(trifluoromethyl)- | 115 |
| 124 | 1H-pyrazole-4-carboxamide, 3-(difluoromethyl)-N-[2-(2,6-dimethyl-1-cyclohexen-1-yl)phenyl]-1-methyl- | 121 |
| 125 | 1H-pyrazole-4-carboxamide, 3-(difluoromethyl)-N-[2-(4-ethyl-1-cyclohexen-1-yl)phenyl]-1-methyl- | 124 |
| 126 | 1H-pyrazole-4-carboxamide, N-[2-(4-ethyl-1-cyclohexen-1-yl)phenyl]-1-methyl-3-(trifluoromethyl)- | 111 |
| 127 | 1H-pyrazole-4-carboxamide, N-[2-(cyclopentylidenemethyl)phenyl]-1-methyl-3-(trifluoromethyl)- | 116 |
| 128 | 1H-pyrazole-4-carboxamide, N-[2-[2-(1-methylethyl)-1-cyclohexen-1-yl]phenyl]-1-methyl-3-(trifluoromethyl)- | 142 |
| 129 | 1H-pyrazole-4-carboxamide, N-[2-(cyclohexylmethyl)phenyl]-3-(difluoromethyl)-1-methyl- | 161 |
| 130 | 1H-pyrazole-4-carboxamide, N-[2-(cyclohexylmethyl)phenyl]-1-methyl-3-(trifluoromethyl)- | 128 |
| 131 | 1H-pyrazole-4-carboxamide, 1-methyl-N-[2-[6-(1-methylethyl)-1-cyclohexen-1-yl]phenyl]-3-(trifluoromethyl)- | Glass at ambient temp. |
| 132 | 1H-pyrazole-4-carboxamide, 3-(difluoromethyl)-N-[2-[4-(1,1-dimethylethyl)-1-cyclohexen-1-yl]phenyl]-1-methyl- | 156–157 |
| 133 | 1H-pyrazole-4-carboxamide, N-[2-[4-(1,-dimethylethyl)-1-cyclohexen-1-yl]phenyl]-1-methyl-3-(trifluoromethyl)- | 155–156 |
| 134 | 1H-pyrazole-4-carboxamide, 3-difluoromethyl)-N-[2-[4-(1,1-dimethylethyl)cyclohexyl]phenyl]-1-methyl- | 152–154 |
| 135 | 1H-pyrazole-4-carboxamide, N-[2-[4-(1,1-dimethylethyl)cyclohexyl]phenyl]-1-methyl-3-(trifluoromethyl)- | 64–66 |
| 136 | 1H-pyrazole-4-carboxamide, N-(3,5-dibromo-2-cyclohexylphenyl)-1-methyl-3-(trifluoromethyl)- | 226–228 |
| 137 | 1H-pyrazole-4-carboxamide, 1-methyl-N-[2-(2-methyl-1-cyclopenten-1-yl)phenyl]-3-(trifluoromethyl)- | 122.5–124 |
| 138 | 1H-pyrazole-4-carboxamide, N-[2-(6-ethyl-2-methyl-1-cyclohexen-1-yl)phenyl]-1-methyl-3-(trifluoromethyl)- | 118.5–120.5 |
| 139 | 1H-pyrazole-4-carboxamide, 1-methyl-N-[2-(3,3,5,5-tetramethylcyclohexyl)phenyl]-3-(trifluoromethyl)- | 147–149 |
| 140 | 1H-pyrazole-4-carboxamide, 3-(difluoromethyl)-1-methyl-N-[2-(3,3,5,5-tetramethylcyclohexyl)phenyl]- | 121.5–123.5 |
| 141 | 1H-pyrazole-4-carboxamide, N-[2-[6-(1,1-dimethylethyl)-1-cyclohexen-1-yl]phenyl]-1-methyl-3-(trifluoromethyl)- | Glass at ambient temp. |
| 142 | 1H-pyrazole-4-carboxamide, N-[2-(cyclopentylmethyl)phenyl]-1-methyl-3-(trifluoromethyl)- | 150 |
| 143 | 1H-pyrazole-4-carboxamide, N-[2-(cycloheptylidenemethyl)phenyl]-1-methyl-3-(trifluoromethyl)- | 106–107 |
| 144 | 1H-pyrazole-4-carboxamide, 3-(difluoromethyl)-N-[2-(5,6-dihydro-2H-thiopyran-4-yl)phenyl]-1-methyl- | 115 |
| 145 | 1H-pyrazole-4-carboxamide, 1-methyl-N-[2-(cycloheptylmethyl)phenyl]-3-(difluoromethyl)- | 132 |
| 146 | 1H-pyrazole-4-carboxamide, 1-methyl-N-[2-(cycloheptylmethyl)phenyl]-3-(trifluoromethyl)- | 125 |
| 147 | 1H-pyrazole-4-carboxamide, N-[2-(cycloheptylidenemethyl)phenyl]-1-methyl-3-(difluoromethyl)- | 116 |
| 148 | 1H-pyrazole-4-carboxamide, N-[2-(3-methyl-1-cyclopenten-1-yl)phenyl]-1-methyl-3-(trifluoromethyl)- | 103–104 |
| 149 | 1H-pyrazole-4-carboxamide, N-[2-(4-methyl-1-cyclopenten-1-yl)phenyl]-1-methyl-3-(difluoromethyl)- | 92 |
| 150 | 1H-pyrazole-4-carboxamide, N-[2-(4-methyl-1-cyclopenten-1-yl)phenyl]-1-methyl-3-(trifluoromethyl)- | 112 |

The compounds of the present invention may be used as is without adding any other components, but generally, they are formulated into emulsifiable concentrates, wettable powders, suspension formulations, granules, dusts, and the like by mixing with a solid or liquid carrier, a surface active agent and other adjuvants for formulation. The compounds of the present invention may also be microencapsulated or otherwise formulated for delayed release of activity.

The content of a compound of the present invention contained as an active ingredient in these formulations is 0.1 to 99.9%, preferably 0.2 to 80% by weight, and more preferably 2 to 50% by weight. The concentration of the active compound in the spray solutions as they are applied to growing plants will be much less, from about 10 ppm up to about 1000 ppm.

The exact amount of active ingredient per hectare to be employed in the treatment or prevention of disease is dependent upon various factors, including the plant species and stage of development of plants and disease, the amount of rainfall, and the specific adjuvants employed. In foliar applications a dosage of from about 10 to about 2000 g/ha, preferably from about 20 to about 250 g/ha, is usually employed. In soil applications a dosage of from about 100 to about 2000 g/ha, preferably from about 250 to about 500 g/ha is usually employed. Lower or higher rates may be required in some instances. One skilled in the art can readily determine from this specification, including the following examples, the optimum rate to be applied in any particular case.

The solid carriers include, for example, fine powders or granules of kaolin clay, attapulgite clay, bentonite, acid clay, pyrophyllite, talc, diatomaceous earth, calcite, corn starch powder, walnut shell powder, urea, ammonium sulfate, synthetic hydrated silicon dioxide, and the like. The liquid carrier includes, for example, aromatic hydrocarbons such as xylene, methylnaphthalene and the like, alcohols such as isopropanol, ethylene glycol, cellosolve and the like, ketones such as acetone, cyclohexanone, isophorone and the like, vegetable oils such as soybean oil, cotton seed oil and the like, dimethyl sulfoxide, acetonitrile, water, and the like.

The surface active agents used for emulsification, dispersion, wetting, etc, include, for example, anionic surface active agents, such as salts of alkyl sulfate, alkyl or aryl sulfonates, dialkylsulfosuccinates, salts of polyoxyethylene alkyl aryl ether phosphoric acid esters, or naphthalenesulfonic acid/formalin condensates, etc, and nonionic surface active agents, such as polyoxyethylene alkyl ether, polyoxyethylene-polyoxypropylene block copolymers, sorbitan fatty acid esters, or polyoxyethylene sorbitan fatty acid esters, etc. Other adjuvants for formulation include, for example, xanthan gum, lignosulfonates, alginates, polyvinyl alcohol, gum arabic, and CMC (carboxymethyl cellulose).

The compounds of the present invention may also be combined with other fungicides, plant growth regulators, fertilizers, herbicides, and insecticides. Penetrating agents, to increase systemic activity may also be added to the compounds of the present invention.

Diseases for which the compounds of the present invention may be used include, but are not limited to, those caused by species of Rhizoctonia, Botrytis, Septoria, Alternaria, Cercosporidium, Pseudocercosporella, Monilinia, Sphaerotheca, Uncinula, Erysiphe, Puccinia, and Venturia.

Crops on which the compounds may be used include, but are not limited to, cereals, for example, wheat, rye, barley, and rice; fruits, for example, apples and grapes; vegetables, for example, eggplants, cucumbers, and tomatoes; oil-producing crops, for example, peanuts, soybeans, and oilseed rape; and turf. Application methods to be used in fungal control on plants include, but are not limited to, direct application to the body of the plant by spraying or other direct application means; soil treatment prior to or at the time of planting, or at any time during the life of the plant; and application to the seed or seed pieces prior to or at the time of planting. The latter two means expose the rhizosphere of the plant to the treatment compound.

The compounds of the present invention have been tested for fungicidal effectiveness in a variety of tests. They have demonstrated exceptionally high levels of control of ascomycete disease such as Botrytis as demonstrated in an enzyme inhibition test as well as in vivo tests. They also have good activity against Rhizoctonia solani as shown below. The compounds have been compared to carboxin and Compound No. 12 of U.S. Pat. No. 4,134,987 (Huppatz, Jan. 16, 1979), the full text of which is incorporated herein by reference, believed to be the closest compound of the prior art. This known fungicide, N-(2-methylphenyl)-1,3,5-(trimethyl)-4-pyrazolecarboxamide, is hereinafter designated Compound H. The following examples describe the tests conducted and the results thereof.

EXAMPLE 1

Enzyme Inhibition

Mitochondria were isolated by a method adapted from G.A. White [Biochem. Biophys. Res. Commun. 44: 1212, 1971]. Twenty to thirty grams of Botrytis cinerea isolate Nick were resuspended in 250 mL 0.25M sucrose, 5mM Na$_4$EDTA, pH 7.0 (+) 0.15% (w/v) bovine serum albumin (BSA) and placed in a Bead Beater chamber (Biospec Products, Bartlesville, Ok.). Zirconium oxide beads (0.5mm) were added to finish filling the chamber. Four 30 second beats separated by 2 minute temperature equilibration periods in the cold were used to break the mycelia. A crude mitochondrial preparation was harvested from the homogenate by differential centrifugation at 4° C. and resuspended in BSA-free sucrose/EDTA media and used for SDH assays.

The succinate dehydrogenase activity was measured at 600 nm in 50 mM potassium phosphate, pH 7.2, 1 mM KCN, 45 $\mu$M 2,6-dichlorophenolindophenol (DCPIP) and 17 mM disodium succinate (final volume, 1 mL) with a Perkin-Elmer Lambda 7 ultraviolet-visible spectrophotometer. The test compounds were added as acetone solutions (final concentration of acetone, 1% (v/v)). The mitochondrial preparatons were used to initiate the reaction. All rates were corrected for endogenous activities minus succinate. Semilog plots of percentage inhibition versus test compound concentration were used to determine inhibition expressed as $I_{50}$ ($\mu$M) which is the concentration required to inhibit the rate of DCPIP reduction by 50%. The commercial fungicide carboxin was used as standard throughout.

The results of this assay for the compounds of the present invention are reported in Table 1.

TABLE 1

| Example Number | $I_{50}$ ($\mu$M conc.) |
|---|---|
| 1 | 0.0095 |
| 2 | 0.012 |
| 3 | 0.027 |
| 4 | 0.065 |
| 5 | 0.0066 |
| 6 | 0.25 |
| 7 | 0.0072 |
| 8 | 0.016 |
| 9 | 0.0019 |
| 10 | 0.003 |
| 11 | 0.0054 |
| 12 | 0.0089 |
| 13 | 0.011 |
| 14 | 0.29 |
| 15 | 0.014 |
| 16 | 0.024 |
| 17 | 0.0063 |
| 18 | 0.031 |
| 19 | 0.028 |
| 20 | 0.014 |
| 21 | 0.019 |
| 22 | 0.0071 |
| 23 | 0.01 |
| 24 | 0.0012 |
| 25 | 0.0011 |
| 26 | 0.0017 |
| 27 | 0.0048 |
| 28 | 0.01 |
| 29 | 0.036 |
| 30 | 0.34 |
| 31 | 0.068 |
| 32 | 0.11 |
| 33 | 0.0014 |
| 34 | 0.0059 |
| 35 | 0.012 |
| 36 | 0.021 |
| 37 | 0.0048 |
| 38 | 0.014 |
| 39 | 0.36 |
| 40 | 0.079 |
| 41 | 0.021 |
| 42 | 0.2 |
| 43 | 0.38 |
| 44 | 0.052 |
| 45 | 0.092 |
| 46 | 0.096 |
| 47 | 0.16 |
| 48 | 0.02 |
| 49 | 0.047 |

TABLE 1-continued

| Example Number | $I_{50}$ (μM conc.) |
|---|---|
| 50 | 0.098 |
| 51 | 0.023 |
| 52 | 0.049 |
| 53 | 0.021 |
| 54 | 0.011 |
| 55 | 0.027 |
| 56 | 0.013 |
| 57 | 0.0047 |
| 58 | 0.0086 |
| 59 | 1 |
| 60 | 0.35 |
| 61 | 0.19 |
| 62 | 0.29 |
| 63 | 0.0063 |
| 64 | 0.047 |
| 65 | 0.011 |
| 66 | 0.048 |
| 67 | 0.056 |
| 68 | 0.0037 |
| 69 | 0.033 |
| 70 | 0.012 |
| 71 | 0.046 |
| 72 | 0.031 |
| 73 | 0.0076 |
| 74 | 0.090 |
| 75 | 0.013 |
| 76 | 0.032 |
| 77 | 22 |
| 78 | 8.7 |
| 79 | 0.011 |
| 80 | 0.083 |
| 81 | 0.38 |
| 82 | 0.065 |
| 83 | 0.13 |
| 84 | 0.013 |
| 85 | 0.01 |
| 86 | 0.0063 |
| 87 | 0.059 |
| 88 | 0.035 |
| 89 | 0.021 |
| 90 | 0.79 |
| 91 | 0.078 |
| 92 | 0.062 |
| 93 | 0.044 |
| 94 | 0.074 |
| 95 | 0.64 |
| 96 | 0.43 |
| 97 | 0.59 |
| 98 | 0.8 |
| 99 | 0.065 |
| 100 | 0.19 |
| 101 | 1.4 |
| 102 | 16 |
| 103 | 0.52 |
| 104 | 0.77 |
| 105 | 0.26 |
| 106 | 0.094 |
| 107 | 0.055 |
| 108 | 1.6 |
| 109 | 0.0072 |
| 110 | 0.019 |
| 111 | 0.0038 |
| 112 | 0.0021 |
| 113 | 0.013 |
| 114 | 0.0036 |
| 115 | 0.0065 |
| 116 | 0.048 |
| 117 | 0.17 |
| 118 | 0.029 |
| 119 | 0.0035 |
| 120 | 0.0041 |
| 121 | 0.0069 |
| 122 | 0.034 |
| 123 | 0.023 |
| 124 | 0.013 |
| 125 | 0.005 |
| 126 | 0.0066 |
| 127 | 0.083 |
| 128 | 1.3 |
| 129 | 0.11 |
| 130 | 0.37 |
| 131 | 0.19 |
| 132 | 0.0035 |
| 133 | 0.0046 |
| 134 | 0.0047 |
| 135 | 0.01 |
| 136 | ** |
| 137 | 0.02 |
| 138 | 0.13 |
| 139 | 0.032 |
| 140 | 0.039 |
| 141 | 0.049 |
| 142 | 0.22 |
| 143 | 0.025 |
| 144 | 0.037 |
| 145 | 0.025 |
| 146 | 0.053 |
| 147 | 0.02 |
| 148 | 0.027 |
| 149 | 0.013 |
| 150 | 0.026 |
| Carboxin | *0.72 ± 0.3 |
| Compound H | 475 |

*Average of 24 determinations.
**Not determined due to limited solubility in medium.

EXAMPLE 2

Eggplant grey mold

Eggplant seed are planted in 2.25" square pots, six per pot, and maintained in growth chambers set at 23° C., 80% humidity, and 12 h photoperiod. When the plants are at the cotyledon stage (14–18 days afterplanting), the plants are sprayed with 1.5 mL/pot of 500, 100 or 20 ppm 2:3 acetone:water (with 0.5% Tween ® 20) formulations of the test compounds.

Twenty-four hours later the plants are inoculated with *Botrytis cinerea*, approximately 0.5 mL/pot of a $4 \times 10^6$ spore/mL suspension. The plantes are incubated at 23° C. and 100% humidity for 3-4 days, at which time disease control ratings are made based on presence and severity of Botrytis lesions. The ratings use the following scale:

0 = No disease control
1 = Low level of control
2 = Moderate control
3 = High level of control The results of this test for compounds of the present invention are reported in Table 2.

TABLE 2

| Compound Number | Disease Control Rating at 500/100/20 ppm |
|---|---|
| 1 | 3/3/3 |
| 2 | 3/3/1 |
| 3 | 2/1/0 |
| 4 | 2/2/1 |
| 5 | 3/3/1 |
| 6 | 1/—/— |
| 7 | 0/—/— |
| 8 | 0/—/— |
| 9 | 2/2/0 |
| 10 | 2/2/2 |
| 11 | 3/2/2 |
| 12 | 3/1/1 |
| 13 | 3/1/1 |
| 14 | 0/—/— |
| 15 | 2/3/2 |
| 16 | 1/—/— |
| 17 | 2/2/1 |
| 18 | 0/—/— |
| 19 | 3/2/1 |
| 20 | 3/2/1 |
| 21 | 2/2/1 |

TABLE 2-continued

| Compound Number | Disease Control Rating at 500/100/20 ppm |
|---|---|
| 22 | 0/—/— |
| 23 | 0/—/— |
| 24 | 2/2/1 |
| 25 | 2/2/1 |
| 26 | 1/2/1 |
| 27 | 2/1/0 |
| 28 | 2/1/0 |
| 29 | 0/—/— |
| 30 | 2/2/0 |
| 31 | 0/0/0 |
| 32 | 2/1/0 |
| 33 | 2/1/1 |
| 34 | 2/2/0 |
| 35 | 3/3/2 |
| 36 | 0/—/— |
| 37 | 2/0/0 |
| 38 | 2/2/0 |
| 39 | 1/—/— |
| 40 | 1/0/0 |
| 41 | 3/0/0 |
| 42 | 0/—/— |
| 43 | 0/—/— |
| 44 | 1/—/— |
| 45 | 0/—/— |
| 46 | 0/—/— |
| 47 | 0/—/— |
| 48 | 0/—/— |
| 49 | 0/—/— |
| 50 | 0/—/— |
| 51 | 0/—/— |
| 52 | 0/—/— |
| 53 | 0/—/— |
| 54 | 0/—/— |
| 55 | 0/—/— |
| 56 | 0/—/— |
| 57 | 0/—/— |
| 58 | 2/0/0 |
| 59 | 0/—/— |
| 60 | 0/—/— |
| 61 | 1/—/— |
| 62 | 1/0/0 |
| 63 | 1/—/— |
| 64 | 2/1/1 |
| 65 | 2/1/0 |
| 66 | 2/0/0 |
| 67 | 2/1/0 |
| 68 | 1/—/— |
| 69 | 0/—/— |
| 70 | 3/2/1 |
| 71 | 0/—/— |
| 72 | 0/—/— |
| 73 | 0/—/— |
| 74 | 1/0/0 |
| 75 | 0/—/— |
| 76 | 0/—/— |
| 77 | 2/1/0 |
| 78 | 2/1/1 |
| 79 | 2/1/0 |
| 80 | 0/—/— |
| 81 | 0/—/— |
| 82 | 0/—/— |
| 83 | 2/0/0 |
| 84 | 2/1/0 |
| 85 | 2/1/0 |
| 86 | 0/—/— |
| 87 | 0/—/— |
| 88 | 0/—/— |
| 89 | 0/—/— |
| 90 | 0/0/0 |
| 91 | 0/—/— |
| 92 | 0/—/— |
| 93 | 0/0/0 |
| 94 | 0/—/— |
| 95 | 0/—/— |
| 96 | 0/—/— |
| 97 | 1/0/0 |
| 98 | 0/—/— |
| 99 | 1/—/— |
| 100 | 0/—/— |
| 101 | 0/—/— |
| 102 | 1/—/— |
| 103 | 0/—/— |
| 104 | 0/—/— |
| 105 | 1/0/0 |
| 106 | 0/—/— |
| 107 | 0/—/— |
| 108 | 0/—/— |
| 109 | 0/—/— |
| 110 | 2/2/1 |
| 111 | 1/1/1 |
| 112 | 3/3/2 |
| 113 | 3/1/1 |
| 114 | 2/1/0 |
| 115 | 3/2/1 |
| 116 | 1/0/0 |
| 117 | 2/1/0 |
| 118 | 0/—/— |
| 119 | 2/1/0 |
| 120 | 2/0/0 |
| 121 | 1/0/0 |
| 122 | 2/2/1 |
| 123 | 0/0/0 |
| 124 | 2/1/0 |
| 125 | 2/1/2 |
| 126 | 1/1/0 |
| 127 | 1/0/0 |
| 128 | 0/0/0 |
| 129 | 0/0/0 |
| 130 | 0/0/0 |
| 131 | 0/0/0 |
| 132 | 0/—/— |
| 133 | 1/0/0 |
| 134 | 2/1/1 |
| 135 | 2/1/1 |
| 136 | 1/0/0 |
| 137 | 3/3/1 |
| 138 | 0/0/0 |
| 139 | 0/0/0 |
| 140 | 1/1/0 |
| 141 | 1/0/0 |
| 142 | 1/1/0 |
| 143 | 0/0/0 |
| 144 | 1/0/0 |
| 145 | 0/0/0 |
| 146 | 1/0/0 |
| 147 | 0/0/0 |
| 148 | 2/2/0 |
| 149 | 1/0/0 |
| 150 | 2/0/0 |
| Carboxin | 0/—/— |
| Compound H | 0/—/— |

— = no test

EXAMPLE 3

Vine grey mold

Grape berries, which have been washed and surfaced sterilized in 70% ethanol for one minute, are, except for the negative controls, treated with 0.2 mL of a 2:3 acetone/water formulation (containing 0.05% Tween ® 20) of 200 or 50 ppm of the test compounds and placed one per well in 12-well plates. Six berries per treatment level are used. Twenty-four hours later each berry is inoculated with Botrytis cinerea conidia, 0.2 mL of $10^6$ spores/mL suspension. The plates are incubated at 20° C. with a 12 hours photoperiod for 7-10 days and the percent surface area infected with the disease is determined for each replicate using the values of 0, 1, 2, 5, 7, 10, 15, 20, 25, 30, 35, 40, 45, 50, 55, 60, 65, 70, 75, 80, 85, 90, 95, and 100%. Treatment means are calculated and percent disease control is determined by the formula [(control mean - treatment mean)/control means]×100.

The results of this test, reported as the average of six berries per treatment level are shown in Table 3. Some of the compounds have been tested more than once and the results shown are the average of the number of tests reported.

TABLE 3

| COMPOUND NUMBER | % DISEASE CONTROL | |
|---|---|---|
| | 200 ppm | 50 ppm |
| 1 | 94* | 92* |
| 2 | 87* | 84* |
| 3 | 62 | 10 |
| 4 | 58* | 29 |
| 5 | 40* | 50* |
| 6 | 20 | 0 |
| 7 | 86* | 72* |
| 8 | 83 | 37 |
| 9 | 89* | 94* |
| 10 | 85* | 87* |
| 11 | 92* | 75* |
| 12 | 59 | 58 |
| 13 | 66* | 63* |
| 14 | 0 | 0 |
| 15 | 89* | 36* |
| 16 | 57 | 15 |
| 17 | 95* | 90* |
| 18 | 0 | 0 |
| 19 | 52 | 32 |
| 20 | 81* | 78* |
| 21 | 34* | 40* |
| 22 | 22 | 24 |
| 23 | 66 | 20 |
| 24 | 100 | 87* |
| 25 | 78* | 66* |
| 26 | 100* | 97* |
| 27 | 74* | 80* |
| 28 | 77 | 37 |
| 29 | 54 | 0 |
| 30 | 59* | 75 |
| 31 | 23 | 0 |
| 32 | 5 | 6 |
| 33 | 41 | 34 |
| 34 | 11 | 44 |
| 35 | 46 | 42 |
| 36 | 38 | 14 |
| 37 | 54 | 25 |
| 38 | 14 | 0 |
| 39 | 55 | 50 |
| 40 | 3 | 2* |
| 41 | 37 | 34* |
| 42 | 25 | 0* |
| 43 | 0 | 3* |
| 44 | 37 | 0* |
| 45 | 12 | 7* |
| 46 | 0 | 1* |
| 47 | 0 | 3* |
| 48 | 0 | 10* |
| 49 | 0 | 4* |
| 50 | 22 | 8* |
| 51 | 27 | 16* |
| 52 | 30 | 19* |
| 53 | 70 | 40* |
| 54 | 2 | 2* |
| 55 | 0 | 11* |
| 56 | 70 | 46* |
| 57 | 72 | 53* |
| 58 | 78 | 51* |
| 59 | 0 | 0 |
| 60 | 0 | 0 |
| 61 | 0 | 0* |
| 62 | 0 | 0 |
| 63 | 65 | 34* |
| 64 | 28 | 10* |
| 65 | 85 | 47* |
| 66 | 35 | 32* |
| 67 | 0 | 31* |
| 68 | 89 | 78 |
| 69 | 70 | 30 |
| 70 | 96* | 97* |
| 71 | 57 | 25* |
| 72 | 0 | 0* |
| 73 | 0 | 8* |
| 74 | 0 | 4* |
| 75 | 0 | 6* |
| 76 | 0 | 8* |
| 77 | 82 | 85 |
| 78 | 35 | 35 |
| 79 | 97 | 69 |
| 80 | 0 | 0 |
| 81 | 7 | 0 |
| 82 | 0 | 0 |
| 83 | 55 | 56* |
| 84 | 96 | 93* |
| 85 | 99 | 28 |
| 86 | 82 | 66 |
| 87 | 46* | 61* |
| 88 | 0 | 0 |
| 89 | 13 | 24 |
| 90 | 33 | 0 |
| 91 | 14 | 0 |
| 92 | 30 | 36 |
| 93 | 15 | 0 |
| 94 | 0 | 0 |
| 95 | 26 | 48 |
| 96 | 0 | 0 |
| 97 | 1 | 0 |
| 98 | 0 | 14 |
| 99 | 53 | 27 |
| 100 | 22 | 0 |
| 101 | 16 | 10 |
| 102 | 83* | 88* |
| 103 | 18 | 5 |
| 104 | 48 | 0 |
| 105 | 0 | 6 |
| 106 | 3 | 9 |
| 107 | 49 | 27 |
| 108 | 0 | 12 |
| 109 | 100 | 100* |
| 110 | 100 | 97* |
| 111 | 100 | 99* |
| 112 | 95 | 88* |
| 113 | 60 | 28 |
| 114 | 90 | 78* |
| 115 | 95 | 42* |
| 116 | 68 | 21 |
| 117 | 19 | 80 |
| 118 | 87 | 37 |
| 119 | 84 | 73 |
| 120 | 82 | 60 |
| 121 | 64 | 33 |
| 122 | 79* | 67* |
| 123 | 36 | 14 |
| 124 | 96 | 48 |
| 125 | 93 | 88* |
| 126 | 97 | 59* |
| 127 | 52 | 12 |
| 128 | 0 | 0 |
| 129 | 0 | 7 |
| 130 | 21 | 2 |
| 131 | 0 | 7 |
| 132 | 51* | 50* |
| 133 | 36 | 39 |
| 134 | 61* | 66* |
| 135 | 66 | 52 |
| 136 | 0 | 7 |
| 137 | 100 | 83* |
| 138 | 4 | 0 |
| 139 | 1 | 2 |
| 140 | 12 | 16 |
| 141 | 12 | 12 |
| 142 | 18 | 0 |
| 143 | 36 | 33 |
| 144 | 37 | 15 |
| 145 | 0 | 0 |
| 146 | 0 | 0 |
| 147 | 0 | 0 |
| 148 | 99 | 37 |
| 149 | 100 | 95 |
| 150 | 100 | 40 |
| Carboxin | 0 | 0 |

TABLE 3-continued

| COMPOUND NUMBER | % DISEASE CONTROL | |
|---|---|---|
| | 200 ppm | 50 ppm |
| Compound H | 9* | 5* |

— = no test
*The result reported is the average of more than one test.

EXAMPLE 4

Rice sheath blight.

Rice plants, 11 to 15 days old, are grown in 7.65 cm$^2$ pots. Each plant in the treatment groups is treated by spraying both the foliage and the soil surface, each with 2 mL of a water/acetone/Tween ®20 formulation containing 0.5, 0.1, or 0.02 mg/mL of Compound A. The pots are placed in flood trays which are filled with water to just below the soil line. Two days later, approximately two grams of *Rhizoctonia solani inoculum*, cultured on rice grain for four to eight weeks, is applied to the base of the rice plants in each pot. After 7 days in a 25° C. high humidity growth chamber, each plant is evaluated for the level of disease contro as compared to untreated controls by the following scale and the average of five plants per treatment level is calculated.

0 = No disease control
1 = Low level of disease control
2 = Moderate disease control
3 = High level of disease control The results of this test for compounds of the present invention are reported in Table 4.

TABLE 4

| Compound Number | Disease Control Rating at 0.5/0.1/0.02 mg/mL |
|---|---|
| 1 | 0/0/2 |
| 2 | 3/3/3 |
| 3 | 0/—/— |
| 4 | 0/—/— |
| 5 | 0/—/— |
| 6 | 1/0/0 |
| 7 | 1/—/— |
| 8 | 0/—/— |
| 9 | 3/3/3 |
| 10 | 3/3/2 |
| 11 | 3/3/1 |
| 12 | 2/—/— |
| 13 | 3/3/2 |
| 14 | 1/—/— |
| 15 | 0/—/— |
| 16 | 1/—/— |
| 17 | 3/—/— |
| 18 | 0/—/— |
| 19 | 3/3/1 |
| 20 | 3/3/2 |
| 21 | 1/—/— |
| 22 | 0/—/— |
| 23 | 3/2/1 |
| 24 | 3/3/3 |
| 25 | 1/—/— |
| 26 | 1/—/— |
| 27 | 0/—/— |
| 28 | 0/—/— |
| 29 | 0/—/— |
| 30 | 3/3/2 |
| 31 | 1/—/— |
| 32 | 0/—/— |
| 33 | 3/1/1 |
| 34 | 3/3/2 |
| 35 | 3/3/2 |
| 36 | 0/—/— |
| 37 | 3/3/3 |
| 38 | 1/0/0 |
| 39 | 0/—/— |
| 40 | 0/—/— |
| 41 | 3/3/1 |
| 42 | 3/3/2 |
| 43 | 3/3/2 |
| 44 | 0/—/— |
| 45 | 0/—/— |
| 46 | 3/3/2 |
| 47 | 3/3/1 |
| 48 | 2/—/— |
| 49 | 0/—/— |
| 50 | 2/0/0 |
| 51 | 2/1/0 |
| 52 | 2/2/0 |
| 53 | 3/3/2 |
| 54 | 2/—/— |
| 55 | 0/—/— |
| 56 | 0/—/— |
| 57 | 0/—/— |
| 58 | 2/—/— |
| 59 | 0/—/— |
| 60 | 0/—/— |
| 61 | 0/—/— |
| 62 | 0/—/— |
| 63 | 3/3/2 |
| 64 | 3/3/1 |
| 65 | 3/3/2 |
| 66 | 3/3/3 |
| 67 | 2/—/— |
| 68 | 3/3/2 |
| 69 | 3/2/0 |
| 70 | 0/—/— |
| 71 | 3/3/1 |
| 72 | 0/—/— |
| 73 | 2/—/— |
| 74 | 0/—/— |
| 75 | 0/—/— |
| 76 | 0/—/— |
| 77 | 0/—/— |
| 78 | 0/—/— |
| 79 | 3/3/3 |
| 80 | 3/3/2 |
| 81 | 3/3/3 |
| 82 | 3/3/3 |
| 83 | 3/3/3 |
| 84 | 0/—/— |
| 85 | 3/3/1 |
| 86 | 3/3/3 |
| 87 | 2/—/— |
| 88 | 0/—/— |
| 89 | 0/—/— |
| 90 | 0/—/— |
| 91 | 0/—/— |
| 92 | 2/1/0 |
| 93 | 0/—/— |
| 94 | 0/—/— |
| 95 | 0/—/— |
| 96 | 0/—/— |
| 97 | 0/—/— |
| 98 | 0/—/— |
| 99 | 3/3/2 |
| 100 | 2/1/0 |
| 101 | 3/1/0 |
| 102 | 3/3/3 |
| 103 | 0/—/— |
| 104 | 0/—/— |
| 105 | 0/—/— |
| 106 | 3/3/2 |
| 107 | 3/3/1 |
| 108 | 0/—/— |
| 109 | 3/1/0 |
| 110 | 3/0/0 |
| 111 | 3/3/3 |
| 112 | 0/—/— |
| 113 | 3/3/3 |
| 114 | 3/3/3 |
| 115 | 3/3/3 |
| 116 | 3/1/1 |
| 117 | 0/—/— |
| 118 | 1/—/— |
| 119 | 2/—/— |
| 120 | 3/—/— |
| 121 | 3/3/1 |

| Compound Number | Disease Control Rating at 0.5/0.1/0.02 mg/mL |
|---|---|
| 122 | 0/—/— |
| 123 | 0/—/— |
| 124 | 2/—/— |
| 125 | 3/2/2 |
| 126 | 3/—/— |
| 127 | 2/—/— |
| 128 | 0/—/— |
| 129 | 3/3/3 |
| 130 | 2/—/— |
| 131 | 2/—/— |
| 132 | 3/2/1 |
| 133 | 3/2/1 |
| 134 | 3/3/3 |
| 135 | 3/—/— |
| 136 | 0/—/— |
| 137 | 3/2/1 |
| 138 | 2/—/— |
| 139 | 3/2/2 |
| 140 | 3/2/0 |
| 141 | 3/—/— |
| 142 | 3/—/— |
| 143 | 3/—/— |
| 144 | 3/—/— |
| 145 | 3/—/— |
| 146 | 1/—/— |
| 147 | 2/—/— |
| 148 | 3/—/— |
| 149 | 3/—/— |
| 150 | 3/—/— |
| Carboxin | 3/1/0 |
| Compound H | 0/—/— |

— = no test

Field Tests

The compounds of Examples 1-150 are combined with various adjuvants, carriers, and other additives and applied to vineyards at rates of from 0.01 to 2.0 kg active ingredient per hectare which reduce the incidence of Botrytis compared to untreated fields. The compounds in mixture with various adjuvants, carriers, and other additives are also applied to various vegetables and cereals at rates of from 0.01 to 2.0 kg active ingredient per hectare and reduce the incidence of fungal disease compared to untreated fields.

| COMPOSITION EXAMPLES | Wt. Pct. |
|---|---|
| Suspension Concentrate: | |
| Compound No. 40 | 48.900 |
| Polyoxypropylene-polyoxyethylene block copolymer | 2.550 |
| Sodium Lignin Sulfonate | 2.040 |
| 10% Dimethylpolysiloxane Emulsion | 1.020 |
| 1% Xanthan gum solution | 0.990 |
| Water | 44.500 |
| Emulsifiable Concentrate: | |
| Compound No. 26 | 13.5 |
| Ethoxylated sorbitan (20EO) | 5.0 |
| C9 Aromatics | 81.5 |
| Wettable Powder: | |
| Compound No. 12 | 75.0 |
| Sodium lignin sulfonate | 3.0 |
| Sodium N-methyl-N-oleyl-taurate | 1.0 |
| Kaolinite clay | 21.0 |
| Granule: | |
| Compound No. 5 | 1.0 |
| Propylene glycol | 5.0 |
| Montmorillonite (24/48 mesh) | 94.0 |
| Dust: | |
| Compound No. 15 | 50.0 |
| Graphite | 10.0 |

| COMPOSITION EXAMPLES | Wt. Pct. |
|---|---|
| Kaolinite clay | 40.0 |

While the illustrative embodiments of the invention have been described with particularly, it will be understood that various other modifications will be apparent to and can be readily made by those skilled in the art without departing from the spirit and scope of the invention. Accordingly, it is not intended that the scope of the claims appended hereto to be limited to the examples and descriptions set forth hereinabove but rather that the claims be construed as encompassing all the features of patentable novelty which reside in the present invention, including all features which would be treated as equivalents thereof by those skilled in the art to which the invention pertains.

We claim:

1. A compound of the formula:

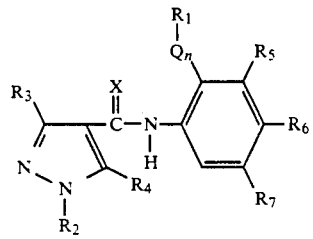

wherein:

Q is C1-C3 alkyl, C2-C3 alkenyl, C2-C3 alkynyl, $-(CH_2)_m CH=$, or $-(CH_2)_m-X-(CH_2)_m-$;

n is 0 or 1;

each m is independently 0, 1, 2, or 3;

each X is independently O or S;

$R_1$ is C3-C12 cycloalkyl, C3-C12 cycloalkenyl, C6-C12 bicycloalkyl, C3-C12 oxacycloalkyl, C3-C12 oxacycloalkenyl, C3-C12 thiacycloalkyl, C3-C12 thiacycloalkenyl, or C3-C12 cycloalkylamine, each of which may be optionally substituted with one or more C1-8 alkyl, C1-8 alkoxy, halo, or cyano groups, provided that when $-Q-R_1$ is $-(CH_2)_m CH=R_1$, the cycloalkyl of $R_1$ is a cycloalkylidene; $R_2$ is hydrogen, fluorinated methyl, methyl, ethyl, C2-C6 alkenyl, C3-C6 cycloalkyl, phenyl, alkylthioalkyl, alkoxyalkyl, haloalkylthioalkyl, haloalkoxyalkyl, or hydroxyalkyl;

$R_3$ is halomethyl, halomethoxy, methyl, ethyl, halo, cyano, methylthio, nitro, aminocarbonyl, or aminocarbonylmethyl;

$R_4$ is hydrogen, halo, or methyl;

$R_5$, $R_6$, and $R_7$ are each independently selected from hydrogen, halo, cyano, C1-6 alkyl, C2-C6 alkenyl, C2-C6 alkynyl, C1-C4 alkoxy, C1-C4 alkylthio, C3-C4 cycloalkyl, and halomethoxy.

2. The compound of claim 1 wherein $R_4$ is hydrogen and $R_3$ is fluorinated methyl.

3. The compound of claim 2 wherein n is O and $R_1$ is C6-C12 cycloalkyl.

4. The compound of claim 2 wherein n is O and $R_1$ is C6-C12 bicycloalkyl.

5. Fungicidal compositions comprising a compound of claim 1 and an adjuvant.

6. The fungicidal composition of claim 5 wherein in said compound $R_4$ is hydrogen and $R_3$ is fluorinated methyl.

7. The fungicidal composition of claim 6 wherein in said compound n is O and $R_1$ is C6-C12 cycloalkyl.

8. The fungicidal composition of claim 6 wherein in said compound n is O and $R_1$ is C6-C12 bicycloalkyl.

9. A method of controlling fungal disease of a plant comprising applying a compound of claim 1 to the plant locus.

10. The method of claim 9 wherein in said compound $R_4$ is hydrogen and $R_3$ is fluorinated methyl.

11. The method of claim 10 wherein in said compound n is O and $R_1$ is C6-C12 cycloalkyl.

12. The method of claim 10 wherein in said compound n is O and $R_1$ is C6-C12 bicycloalkyl.

13. The method of claim 9 wherein said plant locus is the foliage of said plant.

* * * * *